(12) United States Patent  (10) Patent No.: US 8,588,887 B2
Arneson et al.  (45) Date of Patent: Nov. 19, 2013

(54) INGESTIBLE LOW POWER SENSOR DEVICE AND SYSTEM FOR COMMUNICATING WITH SAME

(75) Inventors: Michael R. Arneson, Finksburg, MD (US); William R. Bandy, Gambrills, MD (US); Kevin J. Powell, Annapolis, MD (US); Brian Jamieson, Severna Park, MD (US)

(73) Assignee: Innurvation, Inc., Columbia, MD (US)

( * ) Notice: Subject to any disclaimer, the term of this patent is extended or adjusted under 35 U.S.C. 154(b) by 1358 days.

(21) Appl. No.: 11/851,221

(22) Filed: Sep. 6, 2007

(65) Prior Publication Data

US 2008/0146871 A1  Jun. 19, 2008

Related U.S. Application Data

(60) Provisional application No. 60/842,360, filed on Sep. 6, 2006.

(51) Int. Cl.
*A61B 5/117* (2006.01)
*A61B 5/103* (2006.01)

(52) U.S. Cl.
USPC ............ 600/407; 600/424; 600/437; 600/586

(58) Field of Classification Search
None
See application file for complete search history.

(56) References Cited

U.S. PATENT DOCUMENTS

| | | |
|---|---|---|
| 4,844,076 A | 7/1989 | Lesho et al. |
| 4,987,897 A | 1/1991 | Funke |
| 5,251,326 A | 10/1993 | Silverman |
| 5,265,603 A | 11/1993 | Hudrlik |
| 5,267,033 A | 11/1993 | Hoshino |
| 5,279,607 A | 1/1994 | Schentag et al. |
| 5,329,498 A | 7/1994 | Greenstein |
| 5,395,366 A | 3/1995 | D'Andrea et al. |
| 5,522,865 A | 6/1996 | Schulman et al. |
| 5,528,557 A | 6/1996 | Horn |

(Continued)

FOREIGN PATENT DOCUMENTS

| | | |
|---|---|---|
| DE | 1 261 570 | 2/1968 |
| EP | 1 492 352 A2 | 12/2004 |

(Continued)

OTHER PUBLICATIONS

Yao et al "A wearable point-of-care system for home use that incorporates plug-and-play and wireless standards" IEEE Transaction on information technology in biomedicine, Sep. 2005, 9(3): 363-371.*

(Continued)

*Primary Examiner* — Betty Forman
(74) *Attorney, Agent, or Firm* — Sterne, Kessler, Goldstein & Fox P.L.L.C.

(57) ABSTRACT

Methods, systems, and apparatuses for an ingestible sensor device are described. The ingestible sensor devices may be swallowed by an animal to diagnose one or more conditions of the animal. The ingestible sensor device may include a sensor configured to receive a stimulus inside the gastrointestinal tract of an animal, wherein the sensor is configured to output a signal having a characteristic proportional to the received stimulus. The ingestible sensor device may further include a communications module that transmits a signal modulated with the sensor output signal and a housing configured to have a size that is swallowable, wherein the housing substantially encloses the sensor and communications module.

16 Claims, 15 Drawing Sheets

(56) References Cited

U.S. PATENT DOCUMENTS

| | | |
|---|---|---|
| 5,559,757 A | 9/1996 | Catipovic et al. |
| 5,604,531 A | 2/1997 | Iddan et al. |
| 5,741,311 A | 4/1998 | Mc Venes et al. |
| 5,744,898 A | 4/1998 | Smith et al. |
| 5,792,048 A | 8/1998 | Schaefer |
| 5,794,226 A | 8/1998 | Yoneyama |
| 5,796,827 A | 8/1998 | Coppersmith et al. |
| 5,833,603 A | 11/1998 | Kovacs et al. |
| 5,853,005 A * | 12/1998 | Scanlon ............... 600/459 |
| 5,984,875 A | 11/1999 | Brune |
| 6,076,016 A | 6/2000 | Feierbach |
| 6,104,913 A | 8/2000 | McAllister |
| 6,115,636 A | 9/2000 | Ryan |
| 6,198,965 B1 | 3/2001 | Penner et al. |
| 6,211,799 B1 | 4/2001 | Post et al. |
| 6,239,724 B1 | 5/2001 | Doron et al. |
| 6,240,312 B1 | 5/2001 | Alfano et al. |
| 6,380,858 B1 | 4/2002 | Yarin et al. |
| 6,428,469 B1 | 8/2002 | Iddan et al. |
| 6,431,175 B1 | 8/2002 | Penner et al. |
| 6,486,588 B2 | 11/2002 | Doron et al. |
| 6,504,286 B1 | 1/2003 | Porat et al. |
| 6,577,893 B1 | 6/2003 | Besson et al. |
| 6,584,348 B2 | 6/2003 | Glukhovsky |
| 6,597,320 B2 | 7/2003 | Maeda et al. |
| 6,607,301 B1 | 8/2003 | Glukhovsky et al. |
| 6,628,989 B1 | 9/2003 | Penner et al. |
| 6,702,755 B1 | 3/2004 | Stasz et al. |
| 6,709,387 B1 | 3/2004 | Glukhovsky et al. |
| 6,720,709 B2 | 4/2004 | Porat et al. |
| 6,754,472 B1 | 6/2004 | Williams et al. |
| 6,764,446 B2 | 7/2004 | Wolinsky et al. |
| 6,836,377 B1 | 12/2004 | Kislev et al. |
| 6,845,190 B1 | 1/2005 | Smithwick et al. |
| 6,847,844 B2 | 1/2005 | Sun et al. |
| 6,867,753 B2 | 3/2005 | Chinthammit et al. |
| 6,904,308 B2 | 6/2005 | Frisch et al. |
| 6,934,573 B1 | 8/2005 | Glukhovsky et al. |
| 6,936,003 B2 | 8/2005 | Iddan |
| 6,939,292 B2 | 9/2005 | Mizuno |
| 6,944,316 B2 | 9/2005 | Glukhovsky et al. |
| 6,950,690 B1 | 9/2005 | Meron et al. |
| 6,984,205 B2 | 1/2006 | Gazdzinski |
| 7,009,634 B2 | 3/2006 | Iddan et al. |
| 7,024,248 B2 | 4/2006 | Penner et al. |
| 7,039,453 B2 | 5/2006 | Mullick et al. |
| 7,076,284 B2 | 7/2006 | Segawa et al. |
| 7,104,952 B2 | 9/2006 | Iddan et al. |
| 7,109,859 B2 | 9/2006 | Peeters |
| 7,118,529 B2 | 10/2006 | Glukhovsky et al. |
| 7,118,531 B2 | 10/2006 | Krill et al. |
| 7,119,814 B2 | 10/2006 | Meron et al. |
| 7,122,001 B2 | 10/2006 | Uchiyama et al. |
| 7,135,342 B2 | 11/2006 | Colvin, Jr. et al. |
| 7,140,766 B2 | 11/2006 | Glukhovsky et al. |
| 7,142,908 B2 | 11/2006 | Glukhovsky |
| 7,160,258 B2 * | 1/2007 | Imran et al. ............... 600/593 |
| 7,161,164 B2 | 1/2007 | Glukhovsky |
| 7,195,588 B2 | 3/2007 | Homan et al. |
| 7,200,253 B2 | 4/2007 | Glukhovsky et al. |
| 7,201,872 B2 | 4/2007 | Meron |
| 7,245,954 B2 | 7/2007 | Glukhovsky |
| 7,295,226 B1 | 11/2007 | Meron et al. |
| 7,307,544 B2 | 12/2007 | Kim et al. |
| 7,336,833 B2 | 2/2008 | Horn |
| 7,354,397 B2 | 4/2008 | Fujita et al. |
| 2001/0035902 A1 | 11/2001 | Iddan et al. |
| 2001/0051766 A1 | 12/2001 | Gazdzinski |
| 2002/0107444 A1 | 8/2002 | Adler |
| 2002/0138009 A1 | 9/2002 | Brockway et al. |
| 2002/0165592 A1 | 11/2002 | Glukhovsky et al. |
| 2002/0173718 A1 | 11/2002 | Frisch et al. |
| 2002/0177779 A1 | 11/2002 | Adler et al. |
| 2002/0188323 A1 | 12/2002 | Penner et al. |
| 2002/0193669 A1 | 12/2002 | Glukhovsky |
| 2003/0013370 A1 | 1/2003 | Glukhovsky |
| 2003/0018280 A1 | 1/2003 | Lewkowicz et al. |
| 2003/0043263 A1 | 3/2003 | Glukhovsky et al. |
| 2003/0045790 A1 | 3/2003 | Lewkowicz et al. |
| 2003/0077223 A1 | 4/2003 | Glukhovsky et al. |
| 2003/0114742 A1 | 6/2003 | Lewkowicz et al. |
| 2003/0139661 A1 | 7/2003 | Kimchy et al. |
| 2003/0174208 A1 | 9/2003 | Glukhovsky et al. |
| 2003/0195400 A1 | 10/2003 | Glukhovsky |
| 2003/0195415 A1 | 10/2003 | Iddan |
| 2003/0214579 A1 | 11/2003 | Iddan |
| 2003/0216622 A1 | 11/2003 | Meron et al. |
| 2004/0032187 A1 | 2/2004 | Penner et al. |
| 2004/0032957 A1 * | 2/2004 | Mansy et al. ............... 381/67 |
| 2004/0054278 A1 | 3/2004 | Kimchy et al. |
| 2004/0073087 A1 | 4/2004 | Glukhovsky et al. |
| 2004/0109488 A1 | 6/2004 | Glukhovsky et al. |
| 2004/0114856 A1 | 6/2004 | Kubby et al. |
| 2004/0122315 A1 | 6/2004 | Krill |
| 2004/0162501 A1 | 8/2004 | Imran |
| 2004/0171915 A1 | 9/2004 | Glukhovsky et al. |
| 2004/0181155 A1 | 9/2004 | Glukhovsky |
| 2004/0193029 A1 | 9/2004 | Glukhovsky |
| 2004/0199222 A1 | 10/2004 | Sun et al. |
| 2004/0202339 A1 | 10/2004 | O'Brien, Jr. et al. |
| 2004/0204744 A1 | 10/2004 | Penner et al. |
| 2004/0236182 A1 | 11/2004 | Iddan et al. |
| 2004/0258328 A1 | 12/2004 | Adler |
| 2005/0025368 A1 | 2/2005 | Glukhovsky |
| 2005/0043634 A1 | 2/2005 | Yokoi |
| 2005/0065441 A1 | 3/2005 | Glukhovsky |
| 2005/0075555 A1 | 4/2005 | Glukhovsky et al. |
| 2005/0075559 A1 | 4/2005 | Houzego et al. |
| 2005/0088299 A1 | 4/2005 | Bandy et al. |
| 2005/0110881 A1 | 5/2005 | Glukhovsky et al. |
| 2005/0143624 A1 | 6/2005 | Iddan |
| 2005/0143644 A1 | 6/2005 | Gilad et al. |
| 2005/0148816 A1 | 7/2005 | Glukhovsky et al. |
| 2005/0159643 A1 | 7/2005 | Zinaty et al. |
| 2005/0159789 A1 | 7/2005 | Brockway et al. |
| 2005/0187433 A1 | 8/2005 | Horn et al. |
| 2005/0222490 A1 | 10/2005 | Glukhovsky et al. |
| 2005/0228259 A1 | 10/2005 | Glukhovsky et al. |
| 2005/0256430 A1 | 11/2005 | Lewkowicz et al. |
| 2005/0266074 A1 | 12/2005 | Zilberstein et al. |
| 2005/0272974 A1 | 12/2005 | Iddan |
| 2005/0281446 A1 | 12/2005 | Glukhovsky et al. |
| 2006/0004256 A1 | 1/2006 | Gilad et al. |
| 2006/0009819 A1 | 1/2006 | Von Arx et al. |
| 2006/0045118 A1 | 3/2006 | Hyoung et al. |
| 2006/0074275 A1 | 4/2006 | Davidson et al. |
| 2006/0092908 A1 | 5/2006 | Sung et al. |
| 2006/0116584 A1 | 6/2006 | Sudol et al. |
| 2006/0132599 A1 | 6/2006 | Iddan et al. |
| 2006/0147037 A1 | 7/2006 | Boschetti |
| 2006/0155174 A1 | 7/2006 | Glukhovsky |
| 2006/0158512 A1 | 7/2006 | Iddan et al. |
| 2006/0173361 A1 | 8/2006 | Gorden |
| 2006/0184039 A1 | 8/2006 | Avni et al. |
| 2006/0192889 A1 | 8/2006 | Iddan et al. |
| 2006/0193505 A1 | 8/2006 | Glukhovsky et al. |
| 2006/0252371 A1 | 11/2006 | Yanagida |
| 2007/0002604 A1 | 1/2007 | Lin et al. |
| 2007/0043310 A1 | 2/2007 | Trandafir et al. |
| 2007/0060979 A1 | 3/2007 | Strother et al. |
| 2007/0078335 A1 | 4/2007 | Horn |
| 2007/0123772 A1 | 5/2007 | Euliano et al. |
| 2007/0161851 A1 * | 7/2007 | Takizawa et al. ............. 600/102 |
| 2007/0213659 A1 | 9/2007 | Trovato et al. |
| 2007/0260133 A1 | 11/2007 | Meyer |
| 2007/0282156 A1 | 12/2007 | Konings |
| 2008/0077440 A1 | 3/2008 | Doron |
| 2008/0213355 A1 | 9/2008 | Bohmer |

FOREIGN PATENT DOCUMENTS

| | | | |
|---|---|---|---|
| EP | 1 654 983 | A1 | 5/2006 |
| EP | 1 676 522 | A1 | 7/2006 |
| EP | 1 693 000 | A2 | 8/2006 |

(56) References Cited

FOREIGN PATENT DOCUMENTS

| | | |
|---|---|---|
| EP | 1 698 278 A1 | 9/2006 |
| EP | 1 704 812 A1 | 9/2006 |
| EP | 1 737 124 A2 | 12/2006 |
| GB | 2 414 408 A | 11/2005 |
| WO | WO 01/53792 A2 | 7/2001 |
| WO | WO 02/055126 A2 | 7/2002 |
| WO | WO 02/080753 A2 | 10/2002 |
| WO | WO 02/089913 A2 | 11/2002 |
| WO | WO 03/010967 A1 | 2/2003 |
| WO | WO 03/028224 A2 | 4/2003 |
| WO | WO 03/053241 A2 | 7/2003 |
| WO | WO 2004/014227 A1 | 2/2004 |
| WO | WO 2004/052209 A1 | 6/2004 |
| WO | WO 2004/054430 A2 | 7/2004 |
| WO | WO 2004/058041 A2 | 7/2004 |
| WO | WO 2004/112567 A2 | 12/2004 |
| WO | WO 2005/060348 A2 | 7/2005 |
| WO | WO 2005/062715 A2 | 7/2005 |
| WO | WO 2006/034125 A2 | 3/2006 |
| WO | WO 2006/059331 A2 | 6/2006 |
| WO | WO 2006/103665 A2 | 10/2006 |
| WO | WO 2006/114649 A1 | 11/2006 |
| WO | WO 2006/116718 A2 | 11/2006 |
| WO | WO 2007/028035 A3 | 3/2007 |
| WO | WO 2007/126247 A1 | 11/2007 |
| WO | WO 2007/143200 A2 | 12/2007 |
| WO | WO 2008/014432 A2 | 1/2008 |
| WO | WO 2008/016194 A2 | 1/2008 |

OTHER PUBLICATIONS

Extended European Search Report in re: EP 07837751.2-2319 mailed Aug. 2, 2011.
International Search Report and Written Opinion issued in International Application No. PCT/US2007/019377, mailed Jun. 19, 2008.

* cited by examiner

INGESTIBLE LOW POWER SENSOR DEVICE AND SYSTEM FOR COMMUNICATING WITH SAME

CROSS-REFERENCE TO RELATED APPLICATIONS

The present application claims the benefit of U.S. Provisional Patent Appl. No. 60/842,360, filed Sep. 6, 2006, which is incorporated by reference herein in its entirety.

BACKGROUND OF THE INVENTION

1. Field of the Invention

The present invention relates to medical diagnostics, and in particular, to ingestible medical diagnostic devices.

2. Background Art

The population of the United States is aging. The first wave of the 78 million "Baby Boomers" is beginning to turn 60 years old. Coinciding with this aging of population is a rising concern regarding the public health, and a generally more educated patient in technology awareness. There has been an explosion in diabetes cases, estimated at 194 million cases worldwide today, and predicted to be 350 million cases by year 2025. Obesity currently affects two thirds of the U.S. population. There is a rising incidence of cardiac problems for women (the #1 cause of death for women). Hepatitis C will soon reach epidemic levels, infecting nearly 5 million people, more than the number of approximately 1.2 million people infected with HIV/AIDS in the U.S. Celiac disease affects approximately 2.2 million people in the U.S., with about 97% being undiagnosed. The prevalence of further serious conditions, such as colon cancer, other cancers, ultra- or ulcerative-colitis, lactose intolerance, allergies, irritable bowel syndrome, Crohn's disease, etc., indicate that there is a need for simple and easy diagnostic techniques, especially because many of these diseases are chronic, requiring repeat testing over time. Some conditions, such as cancer, are most responsive to treatment if caught in the early stages. Cancer, for example, is best detected in the digestive tract. Given that cancerous growth can occur in as little as one to two years, it is essential to detect cancer or cancerous precursors at least annually, or preferably biannually. Physician and health care resources are currently already stretched and will fail if the current technology, process and procedure are not altered to suit the needs of the baby boomer market of the near future. Time-saving and simple solutions to diagnostics are needed.

The current population desires speedy testing and fast answers to their health questions. Many current testing and monitoring systems are limited by old technology and processes that takes days if not weeks for results. These test methods if not inconvenient and potentially embarrassing are at least in most cases intrinsically painful or risky to patients.

One ingestible diagnostic device in the market today is a disposable camera pill or capsule camera, which captures images of the small intestines as it passes through. Camera pill usage by patients and physicians is limited in many different ways. The current camera pill systems require a bulky reading device worn as a belt around the waist and adhesive sensors attached to the body to capture the electromagnetic inductively coupled signal sent from the pill. The patient is required to report to a physician's office to initiate use of the camera pill, and to be fitted with the belt reader. The reader belt is worn for 24 hours, during which time the camera pill captures images and transmits the images to the reader belt. At the end of a diagnosis period, the belt reader is returned to the physician. The physician downloads images from the belt reader and analyzes the images. Thus, the camera pill requires at least two trips to the physician's office, as well the wearing of a cumbersome reader belt with leads attached to the skin. This diagnostic process is both inconvenient and uncomfortable. Furthermore, the current camera pill is an expensive device, and is resorted to when other bowel disease diagnostic techniques, such as endoscopy and colonoscopy, present results that need further investigation. Additionally, the camera pill senses visible (white) light spectrum, which is not itself a direct indicator of a specific disease or chemical inbalance. Therefore, the ingestible camera pill has significant deficiencies.

Thus, what is needed are diagnostic devices, services and processes that are simple, convenient, relatively inexpensive, comfortable, take less time, directly detect specific compounds or indicators to disease, and have more applications.

BRIEF SUMMARY OF THE INVENTION

Methods, systems, and apparatuses for ingestible sensor devices are described herein. The ingestible sensor devices may be swallowed by an animal to diagnose one or more conditions of the animal. The ingestible sensor device may include a sensor configured to receive a stimulus inside the gastrointestinal tract of an animal, wherein the sensor is configured to output a signal having a characteristic proportional to the received stimulus. The ingestible sensor device may further include a communications module that transmits an acoustic signal modulated with the sensor output signal and a housing configured to have a size that is swallowable, wherein the housing substantially encloses the sensor and communications module. The ingestible sensor devices may be used in any type of animal, including humans. In addition, these same sensor devices may be temporarily implanted into animals for the purpose of continuous monitoring, such as with a several hour to several day diagnostic period at 'home' or at a professional care center. A sensor link module may be located on the surface of the animal to receive the acoustic signal output by the sensor.

These and other objects, advantages and features will become readily apparent in view of the following detailed description of the invention. Note that the Summary and Abstract sections may set forth one or more, but not all exemplary embodiments of the present invention as contemplated by the inventor(s).

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

Figure 1:
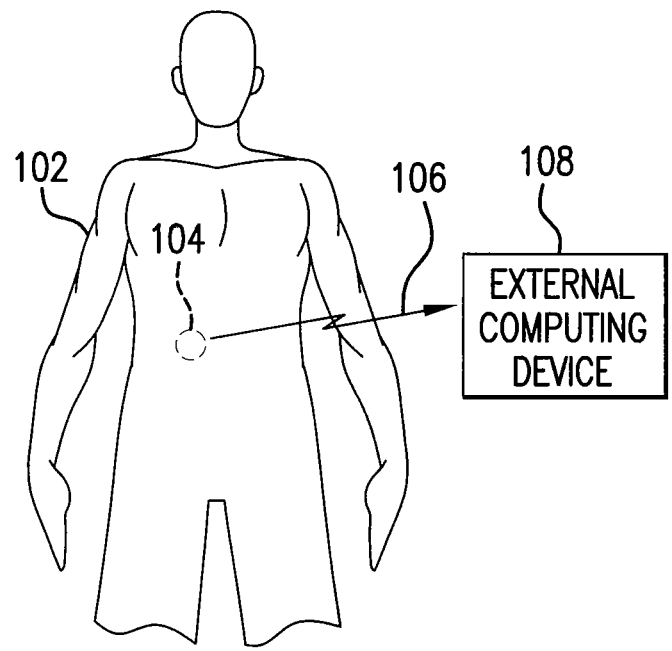
FIG. 1 illustrates a partial view of a human according to an embodiment of the present invention.

The present invention will now be described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE INVENTION

Introduction

Methods, systems, and apparatuses for ingestible sensors are described. Furthermore, methods, systems, and apparatuses for operating and communicating with the ingestible sensors are also described. The present specification discloses one or more embodiments that incorporate the features of the invention. The disclosed embodiment(s) merely exemplify the invention. The scope of the invention is not limited to the disclosed embodiment(s). The invention is defined by the claims appended hereto.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Furthermore, it should be understood that spatial descriptions (e.g., "above," "below," "up," "left," "right," "down," "top," "bottom," "vertical," "horizontal," etc.) used herein are for purposes of illustration only, and that practical implementations of the structures described herein can be spatially arranged in any orientation or manner. Likewise, particular bit values of "0" or "1" (and representative voltage values) are used in illustrative examples provided herein to represent data for purposes of illustration only. Data described herein can be represented by either bit value (and by alternative voltage values), and embodiments described herein can be configured to operate on either bit value (and any representative voltage value), as would be understood by persons skilled in the relevant art(s).

Example Embodiments

The example embodiments described herein are provided for illustrative purposes, and are not limiting. Further structural and operational embodiments, including modifications/alterations, will become apparent to persons skilled in the relevant art(s) from the teachings herein.

Methods, systems, and apparatuses for a ingestible sensor device are described. The ingestible sensor devices may be swallowed by an animal to diagnose or aid in diagnosis of one or more conditions of the animal through either an immediate detection or a historical and/or statistical analysis of multiple detections of conditions or attributes over a time period. Example embodiments are described below as related to a human subject, for illustrative purposes. However, embodiments of the present invention are applicable to further types of animals other than humans, including livestock (cattle, sheep, pigs, chickens, turkeys, ostriches, etc.), pets (e.g., dogs, cats, horses, etc.), and other animals of interest such as race horses or other performance/sport animals. Such applicability to these types of animals, and other types, will be apparent to persons skilled in the relevant art(s) from the teachings herein, and is within the scope and spirit of embodiments of the present invention.

Furthermore, example embodiments are described below as related to passing a ingestible sensor device through a gastrointestinal tract, for illustrative purposes. However, embodiments of the present invention are applicable to further bodily systems other than the gastrointestinal tract, including the circulatory system, the urinary tract, the uterus, and other bodily systems and additionally other means of entry or implant into a body cavity of an animal or human. Such applicability to other types of bodily systems will be apparent to persons skilled in the relevant art(s) from the teachings herein, and is within the scope and spirit of embodiments of the present invention.

For example, FIG. 1 shows a partial view of a human 102 in example application environment 100, according to an embodiment of the present invention. In FIG. 1, human 102 has swallowed or ingested a ingestible sensor device 104. Ingestible sensor device 104 is configured to be swallowable by human 102, and to sense one or more attributes or conditions of human 102 as ingestible sensor device 104 passes through human 102. One or more sensors on ingestible sensor device 104 may be passive in that they do not require power, or they may be active and require power. One or more sensors on ingestible sensor device 104 may be low data rate sensors or high data rate sensors. While passing through human 102, ingestible sensor device 104 transmits information in a communication signal 106 to be received outside human 102. As shown in FIG. 1, an external computing device 108 may receive communication signal 106. Computing device 108 may be used to display the information received in communication signal 106, to interact with the information, to process the information, and/or to transmit the information (raw or processed) to another entity.

In a simplistic embodiment, computing device 108 may simply act as a protocol converter in a store and forward manner. However, in a more complex environment, computing device 108 may perform complex and intensive functions such as data normalization, compression, and encryption for example.

In another advanced embodiment, computing device 108 can interact with ingestible sensor device 104 to control functions of ingestible sensor device 104. This embodiment infers a bi-directional communication 106 with sensor device 104. Bi-directional communications are generally common place with persons skilled in the art. However, these designs are typically designed to be able to receive signals either at times not transmitting, or at all times. These common techniques are not desirable in the described environment as receivers require power, and additional power would consequently add to the size of sensor device 104. External computing device 108 receives and stores commands and/or information from a network. Upon termination of the next transmission from sensor device 104, sensor device 104 may turn on a receiver for a very short amount of time, while external device 108 commences transmission of commands or information to sensor device 104. Greatly reduced power requirements on sensor device 104 are gained from very rapidly turning off a receiver when no communications (or an indication of no information to communicate) are received from device 108 within a defined time window after a last transmission from sensor device 104.

In embodiments, human 102 may be provided with one or more types of ingestible sensor devices 104 that human 102 may at designated times and/or periodically swallow to perform an analysis of one or more health related conditions of human 102.

Figure 2:
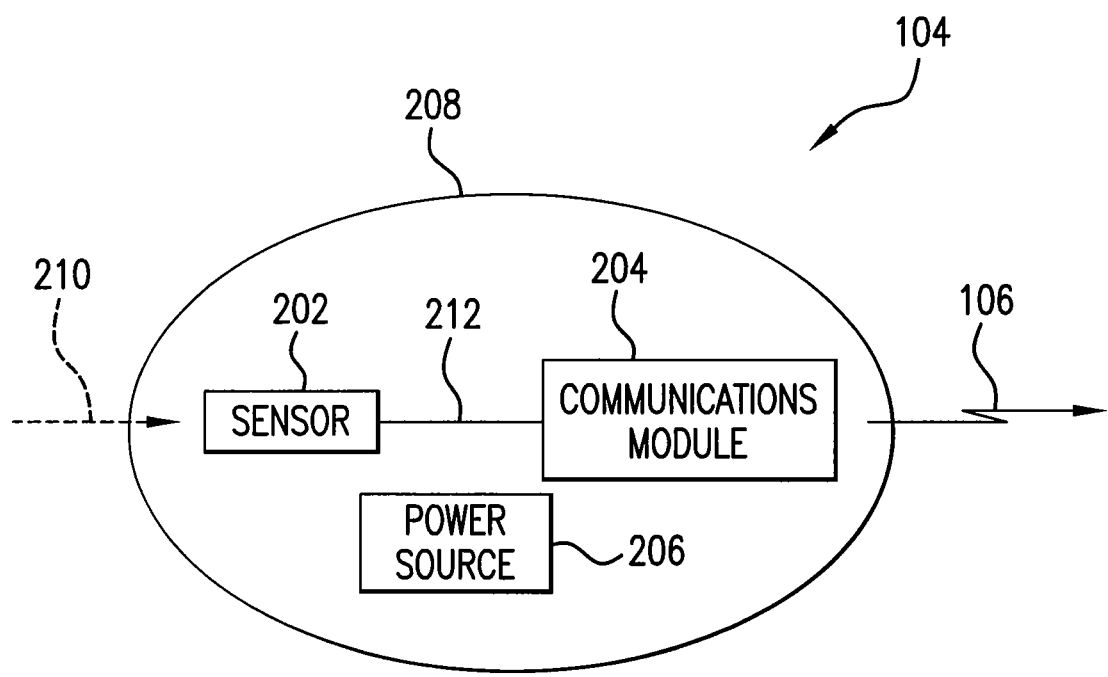
FIG. 2 is a block diagram of an ingestible capsule according to an embodiment of the present invention.

FIG. 2 shows an example block diagram of ingestible sensor device 104, according to an embodiment of the present invention. In FIG. 2, ingestible sensor device 104 includes a housing 208 that encloses a sensor 202, a communications module 204, and a power source 206. Sensor 202 is used to sense (e.g., measure, detect, etc.) a received stimulus 210, and generate a sensor output signal 212. Sensor output signal 212 may be a digital or analog signal, depending on the particular implementation of sensor 202. Sensor 202 is further described below. In alternative embodiments the housing 208 may be comprised of sensor(s) 202, or the sensor(s) 202 may be integrated within the materials known as housing 208.

Communications module 204 receives sensor output signal 212, and generates communication signal 106 to include information based on sensor output signal 212. Communication signal 106 is transmitted from ingestible sensor device 104. Communications module 204 is further described below.

Power source 206 provides power (e.g., via electrical energy) to operate the components of ingestible sensor device 104 that require power, such as communications module 204. Thus, communications module 204 may be coupled to an output power signal from power source 206. In some embodiments, sensor 202 requires power and thus is coupled to the output power signal from power source 206. In other embodiments does not require power and thus is not coupled to the output power signal from power source 206. In yet another embodiment, the power source may be a material, potentially a liquid, surrounding communications module 204.

Figure 27:
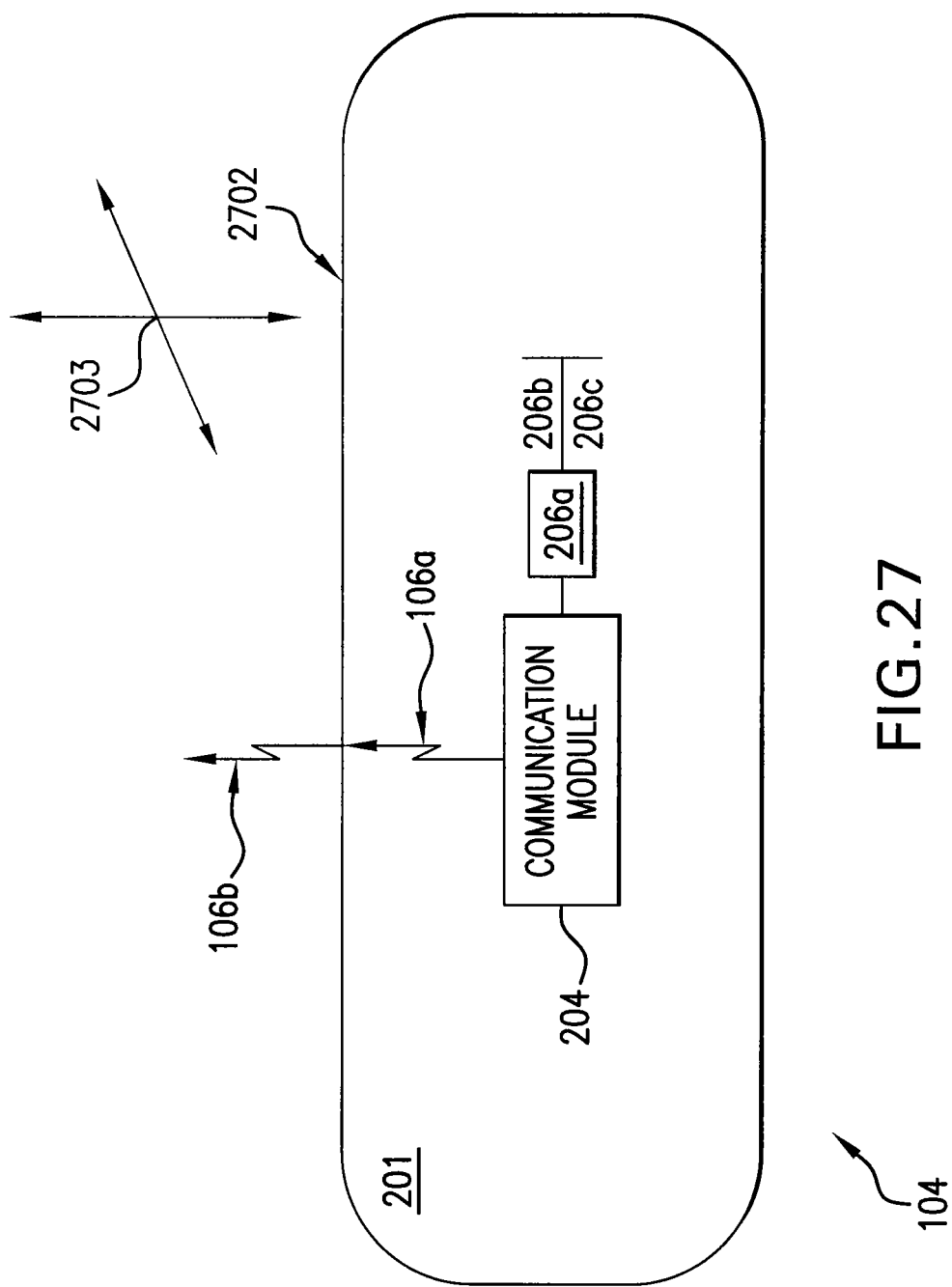
FIG. 27 illustrates a power source for an acoustic transmitter according to an embodiment of the present invention.

In an embodiment, power source 206 includes a liquid or semi-liquid, such as is illustrated in FIG. 27. In this embodiment, communications signal 106 is a signal of acoustic nature, and power source 206 includes an electrolyte 2701 in the form of an acoustically transmissive material such as a liquid or semi-liquid. Electrolyte 2701 serves a first purpose of a battery component but also serves as an efficient medium of acoustic transmission. Furthermore, as illustrated in FIG. 27, a material 2702 serves a dual purpose of housing battery 2701 as well as other components, while allowing an efficient transfer of acoustic energy from inside to outside of ingestible capsule 104. FIG. 27 additionally demonstrates control and regulation component 206a, anode 206b, and cathode 206c.

Communication signals 106 pass through electrolyte 2701 and external animal flesh environment 2703. In the case of an acoustic propagation, the most efficient energy transfer is accomplished when the acoustic material impedance from material to material is gradually changed from origin to destination from high to low, or low to high impedance as is common knowledge to those skilled in the art. Communication signal 106 then is demonstrated in FIG. 27 as a combination of signals 106a and 106b to illustrate the change in medium properties from electrolyte 2701 through housing material 2702 and into flesh 2703. As one example of many, electrolyte 2701 may be a citric juice or gel that is non-harmful to human consumption; anode 206b and cathode 206c may include zinc and copper, which is also not harmful to human consumption; and housing 2702 may be comprised of a thin but soft plastic of reasonable acoustic impedance to electrolyte 2701 and animal flesh 2703. However, other material selections by those skilled in the art of battery technology and acoustic propagation for electrolyte 2701, housing 2702, anode 206b and cathode 206c do not depart from the spirit and scope of this invention.

Housing 208 contains sensor 202, communications module 204, and power source 206, and is configured to be swallowable by or inserted within a human and/or animal. For example, housing 208 may be sized to be able to be swallowed by human 102, to be able to pass through a gastrointestinal tract of human 102, and to be naturally passed by human 102. Housing 208 may be the size of a vitamin or other type of pill that is swallowable by humans. Housing 208 may be any suitable shape, including oval, elliptical (as shown in FIG. 2), capsule shaped, or spherical. Furthermore, housing 208 may be made from a variety of non-digestible or slow rate of digestion materials, including: a plastic material, such as a resin, a resinoid, a polymer, a cellulose derivative, a casein material, and/or a protein; a metal, including a combination of metals/alloy; a glass material; a ceramic; a composite material; and/or other material/combination of materials. In a particular embodiment, housing 208 may be comprised of a material that aids in the sensing of biological, chemical, or other attributes of body material that touches or comes in close proximity to the housing 208, such as could be called an integrated housing and sensor material.

Figure 3:
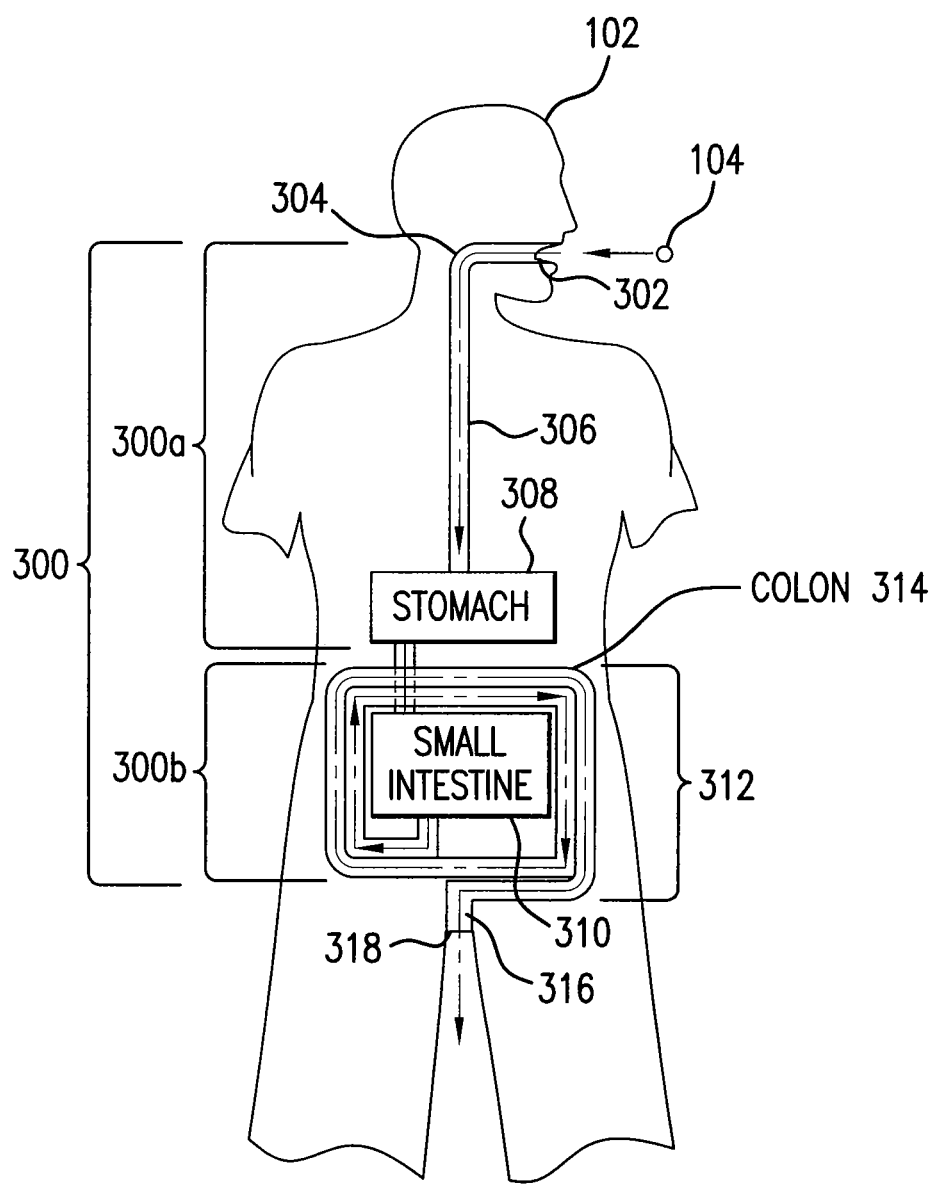
FIG. 3 illustrates a cross-sectional view of a human.

For example, FIG. 3 shows a cross-sectional view of human 102, showing basic details/organs of a gastrointestinal tract 300 of human 102. Gastrointestinal tract 300 includes an upper gastrointestinal tract 300a and a lower gastrointestinal tract 300b. Upper gastrointestinal tract 300a includes a mouth 302, a pharynx 304, an esophagus 306 and a stomach 308. Lower gastrointestinal tract 300b includes a small intestine 310 and a large intestine 312.

Each portion of the gastrointestinal tract 300 includes features known to persons skilled in the relevant art(s). For example, mouth 302 includes features not specifically shown in FIG. 3, such as a buccal cavity, salivary glands, mucosa, teeth and a tongue. Small intestine 310 includes features not specifically shown in FIG. 3, including the duodenum, jejunum, and ileum. Large intestine 312 includes a caecum, a colon 314, a rectum 316, and an anus 318.

Ingestible sensor device 104 may be swallowed by human 102 at mouth 302. Ingestible sensor device 104 passes through mouth 302 past pharynx 304, through esophagus 306, stomach 308, small intestine 310, and large intestine 312. In an average human, gastrointestinal tract 300 is approximately 27 feet. Ingestible sensor device 104 eventually passes from human 102 at anus 318, such as when human 102 has a bowel movement to excrete waste. In an embodiment, ingestible sensor device 104 is disposable. In another embodiment, ingestible sensor device 104 may be recovered, (and recycled) for reuse.

Depending upon the ability or control of the patient, ingestible sensor device 104 may alternatively be inserted into the lower gastrointestinal tract 300b, also known as a suppository device. Suppository use may be utilized in cases where monitoring is desired, but ingestion is not possible. Unconscious, elderly, and newborn babies are examples of human suppository use. Animal suppository use may be more convenient when there is a risk of injury in administering an ingestible device; or when an ingested device has a high likelihood of being damaged or destroyed in the process of ingestion.

Depending on the configuration of sensor 202, while passing through gastrointestinal tract 300, ingestible sensor device 104 can sense conditions and/or features of any of mouth 302, pharynx 304, esophagus 306, stomach 308, small intestine 310, large intestine 312, any of the subcomponents of these organs, and any of the materials/fluids contained within and/or secreted by these organs. For example, with regard to mouth 302, ingestible sensor device 104 can be configured to sense attributes of saliva. With regard to stomach 308, ingestible sensor device 104 can be configured to sense attributes of the digestive juices residing therein. One of many examples would comprise a configuration of sensor 202 that senses the existence and concentration of specific digestive enzymes and/or bacteria, useful for diagnosis of digestive disorders or abnormalities.

In addition to these organs directly associated with gastrointestinal tract 300, ingestible sensor device 104 can be configured to sense features and/or conditions of organs indirectly associated with gastro intestinal tract 300, such as the liver, the gallbladder, and the pancreas (not shown in FIG. 3). For example, the liver secretes bile into small intestine 310 via the biliary system. The gallbladder acts as a reservoir for excess bile. The pancreas secretes an isosmotic fluid containing bicarbonate and several enzymes, including trypsin, chymotrypsin, lipase, and pancreatic amylase, as well as nucleolytic enzymes (deoxyribonuclease and ribonuclease), into small intestine 310. Both these secretory organs (the liver and pancreas) aid in digestion. Sensors 202 of ingestible sensor device 104 can be configured to sense the presence of one or more of these chemicals secreted by the liver and pancreas to diagnose a condition of the liver, gallbladder, and pancreas.

Furthermore, body materials can also carry or relay conditions or signals from even more remote body organs to the sensor device such as is the case with acoustic pickup of heartbeat and/or breathing; and more indirect conditions such as temperature as may be detected utilizing distant material or scanning heat detection devices extending temperature detection past the materials only in contact with ingestible sensor device 104. An example use of scanning heat detection information is the ability to determine very localized high levels of thermal activity in gastrointestinal tract 300. High levels of thermal activity may indicate infection, allergic reaction, rapid cellular growth common with cancer formation, and potentially other abnormalities of interest to the medical profession. Additionally, scanning heat detection allows evaluation of differences in temperature of tissue in general, which can be used to normalize data and thereby greatly reduce the effect of a normal daily increase and decrease in an animal's core temperature.

Figure 4:
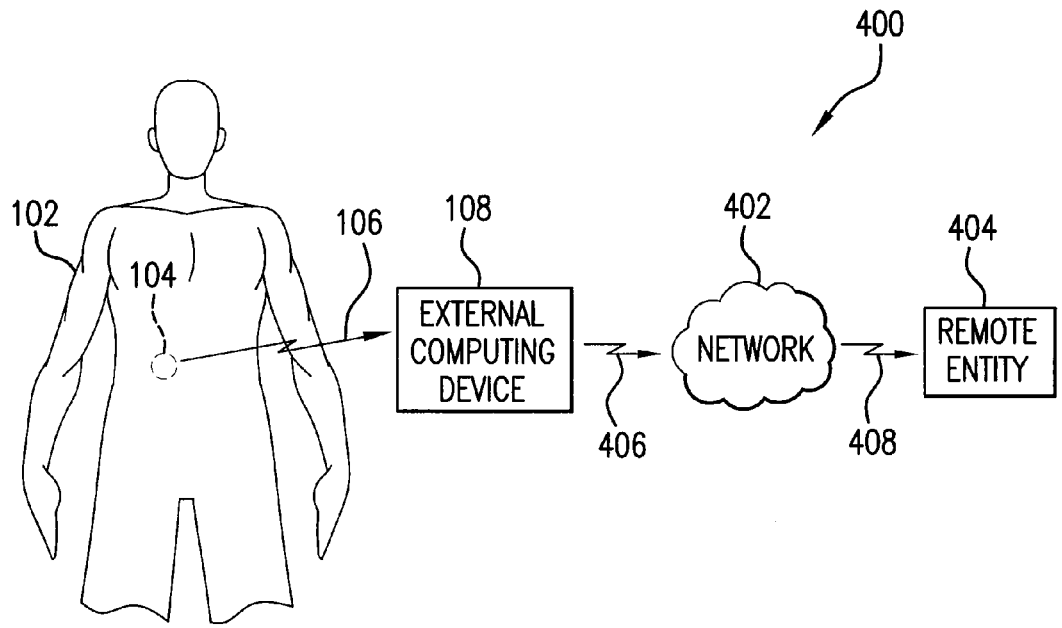
FIG. 4 is a block diagram of a communications network according to an embodiment of the present invention.

As described above, while passing through human 102, ingestible sensor device 104 transmits information in communication signal 106 to be received outside human 102, such as by computing device 108. Furthermore, in an embodiment, computing device 108 may be configured to communicate with a remote entity 404, such as shown in an example sensor communications network 400 shown in FIG. 4. For example, computing device 108 may be configured to communicate with remote entity 404 using wired and/or wireless links, in a direct fashion or through a network 402. FIG. 4 shows an example embodiment, where computing device 108 transmits a communication signal 406 to network 402, which transmits a communication signal 408 to remote entity 404. Network 402 may be any network type or combination of networks, such as a telephone network (such as a land line and/or cellular network), a personal area network (PAN), a local area network (LAN), and/or a wide area network (WAN) such as the Internet. First and second communication signals 406 and 408 may be transmitted through wired and/or wireless links.

Remote entity 404 may be one or more of a variety of entities, including a human and/or computer-based entity. For example, remote entity 404 may include a doctor who receives information collected by ingestible sensor device 104 (and optionally processed by computer device 108) in communication signal 408. The doctor may analyze the information to examine human 102, to diagnose a condition of human 102, including as part of performing a routine physical exam, and/or actually diagnosing an adverse condition (e.g., disease, illness, deficiency, etc.) of human 102. In addition or alternatively, remote entity 404 may include a computer system that is configured to analyze the information received in communication signal 408 to diagnose a condition of human 102. In an embodiment, the information is received in communication signal 408 in a format in which the computer system of remote entity 404 can perform an automated analysis of the information to diagnose a condition of human 102. In an embodiment, both the doctor and computer system perform their respective analysis, to provide an increased quality of the examination of human 102, and a resulting increase in a probability detecting health problems and/or maintaining a health of human 102 at a high level.

Network 402 may have multiple remote entities 404 performing a variety of potentially dependent functions on data retrieved and stored within network 402. For example, raw data collected by devices 104 and 108 may be stored within network 402. Remote entity/process 404(a) may normalize data and restore this onto network 402. Remote entity/process 404(b) may interpret and annotate data and store analysis on network 402. Remote entity/process 404(c) may perform diagnosis of data stored on network 402. Remote entity/process 404(d) may perform industry billing methods based upon data stored on network 402. Other additions of entities and/or processes 404 known to one of skill in the art may be used without departing from the spirit and scope of the present invention.

Figure 5:
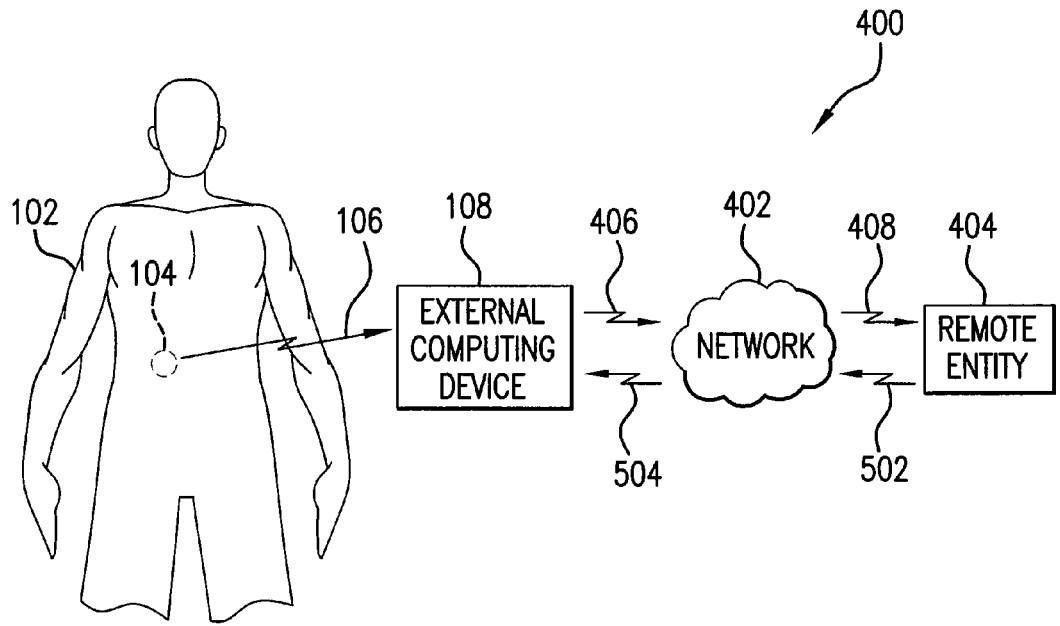
FIG. 5 is another block diagram of a communications network according to an embodiment of the present invention.

Furthermore as shown in FIG. 5, sensor communications network 400 may include a return communications path from remote entity 404 through network 402 to computing device 108. For example, FIG. 5 shows a return communication signal 502 transmitted by remote entity 404 to network 402, which transmits a return communication signal 504 to computing device 108. In this manner, remote entity 404 (e.g., doctor and/or computer system) can provide feedback to computing device 108 in communication signal 504 regarding the analysis of human 102 performed by ingestible sensor device 104. Return communication signal 504 may include any type of data/information format for providing the feedback, including an email, a text message, a text file, a document formatted for commercially available word processing software, a proprietary document/data format, auditory alarms, digitized audio such as mp3 clips and ring tones, alerts and messages, etc. In an embodiment, a network conveying signals from external computing device 108 to entity 404 via paths 406 and 408 may be a different network that the network located in the return path (paths 502 and 504) from entity 404 to external computing device 108. An example of this includes a cellular data connection for communications from external computing device 108 to remote entity 404, whereas a voice network call may be returned from remote entity 404 to external computing device 108. In a more complex network application environment, external device 108 may send information into network 402, and having multiple remote entities 404 interconnected ia network 402, an first remote entity may forward new information to a second remote entity, thereby prompting the second remote entity to return a signal, such as signal 502, through network 402 to external computing device 108. An example of such a complex network structure is an external computing device 108 directly sending information to an interpretation service (a first remote entity), which sends results to a doctor's office (a second remote entity) via network 402. Subsequently, the doctor's office performs a final diagnosis and returns message 502 to external computing device 108. One of skill in the art will recognize that other such complex network schemes may be used without departing from the spirit and scope of the present invention.

The provided feedback 502 and 504 may include information to be displayed on computing device 108 for viewing by human 102 (and/or other person such as family member of human 102, local caregiver, etc.). The feedback may include a prescription for medication for human 102, and instructions for taking the medication. Such feedback may be also provided to a pharmacist in order to fill a prescription for human 102, without a need for human 102 to provide the prescription to the pharmacist. Computing device 108 may enable human 102 to authorize the prescription to be filled by the pharmacist, by interacting with an interface of computing device 108, such as a keyboard-based, a computer mouse, touch pad, joystick, voice activated, graphical user interface (GUI), etc., to provide the authorization. In other applications, provided feedback may include indication of action required at a specific time, such as an indication to administer medicine, a need to ingest another swallowable sensor, an immediate health warning such as to lower elevated core body temperatures, or a very useful indication of ideal conditions for a couple to conceive.

The provided feedback may include an appointment for human 102 to see a doctor (such as the doctor of remote entity 404). The feedback may include health information, including an activity that human 102 may perform to improve their health and/or to further diagnose their condition. For example, the feedback may include exercise and/or diet instructions. The feedback may include information on taking one or more further ingestible sensor devices 104 as a follow-up analysis to the prior taken ingestible sensor device(s) 104, including re-performing a similar analysis with a ingestible sensor device 104 having a same type sensor 202 and/or performing a different analysis with a ingestible sensor device 104 having a different ingestible sensor device 104. The feedback may include software downloads for computing device 108 and/or ingestible sensor device 104 to improve/change a function of computing device 108 and/or ingestible sensor device 104.

Further examples of computing device 108 are described further below.

Figure 6:
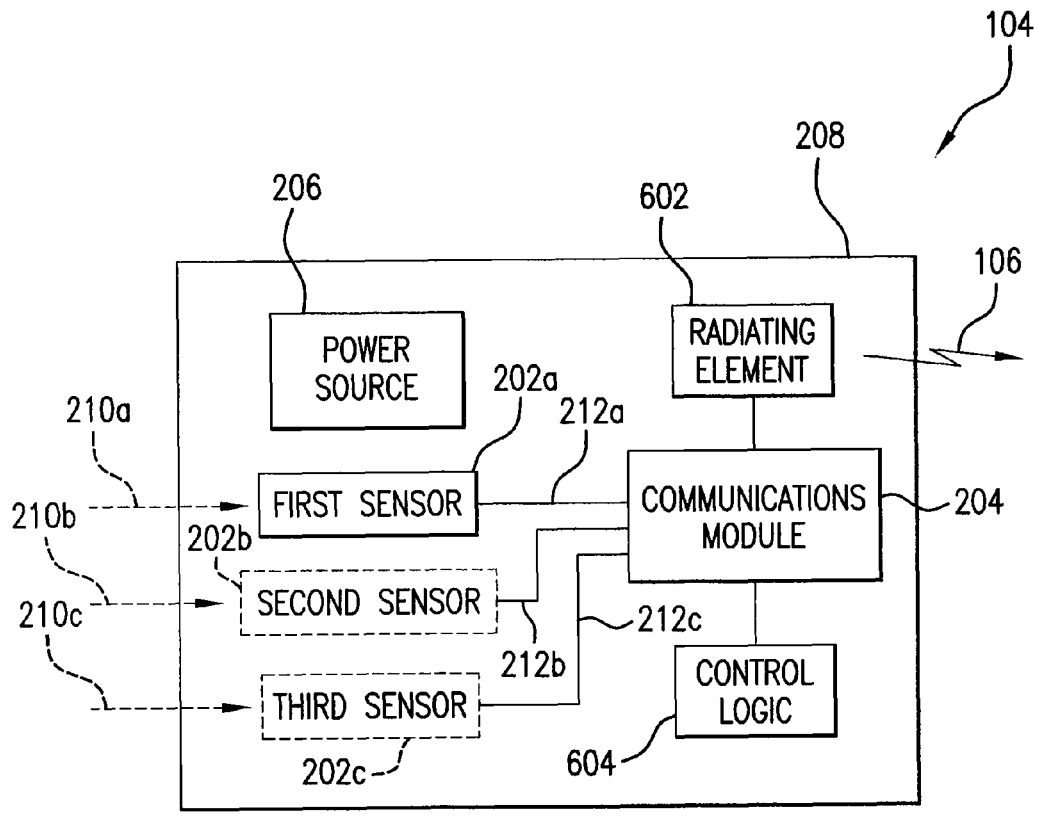
FIG. 6 is a block diagram of an ingestible capsule according to another embodiment of the present invention.

In embodiments, ingestible sensor device 104 can be configured in a variety of ways. For instance, FIG. 6 shows an example embodiment of ingestible sensor device 104. As shown in FIG. 6, ingestible sensor device 104 includes housing 208 that encloses a plurality of sensors 202a-202c, communications module 204, and power source 206, a radiating element 602, and a control logic 604.

Ingestible sensor device 104 can include any number of one or more sensors 202, including two sensors, or three sensors 202a-202c as shown in FIG. 6. In the example of FIG. 6, each of sensors 202a-202c receives a corresponding one of stimuli 210a-210c, and generates a corresponding sensor output signal 212a-212c, which are received by communications module 204. In embodiments, ingestible sensor device 104 can include numbers of sensors 202 in the tens or even hundreds of sensors 202. Each sensor 202 can be configured to sense a different condition. Alternatively, one or more of sensors 202 can be configured to sense the same condition, at the same time for redundancy purposes or at timed release intervals responsive to stimuli 210, to sense rare conditions/chemicals, as a failsafe measure, and/or for further purposes. Thus, in an embodiment where multiple sensors 202 are present that are configured to sense multiple conditions, ingestible sensor device 104 can perform as a general purpose diagnostic device. Alternatively, ingestible sensor device 104 may include one or just a few types of sensors 202 to perform as a special purpose diagnostic device, such as to diagnose a specific condition.

In a further embodiment, to extend the overall operational time of sensor device 104 for a much longer period than the operational time of an individual sensor 202, timed release coatings protecting sensors 202 from stimuli 210 and other materials such as stomach acid, for example, will ensure that at any one time at least one of sensors 202 are fully operational and exposed to stimuli 210. An example of a short life sensor is a biological enzyme based sensor 202, which includes an applied enzyme substance over an electrical surface. Such a sensor would typically be destroyed in stomach acid, making the sensor non-functional upon entry into the small bowels. Without a timed release configuration or coating, the whole of sensor device 104 would be rendered useless for the continued sensing of stimuli 210, for example a blood detector 202, as device 104 continues through the majority of digestive system 300b. Furthermore, control logic 604 may sense which of sensors 202 have valid operational ranges on signals 212 and either only allow communications module access to a valid operational range of sensor 202, or potentially discontinue use by communications module 204 of an out of range signal 212 and/or discontinue power supplied by source 206 to an out of range sensor 202.

Figures 7, 8:
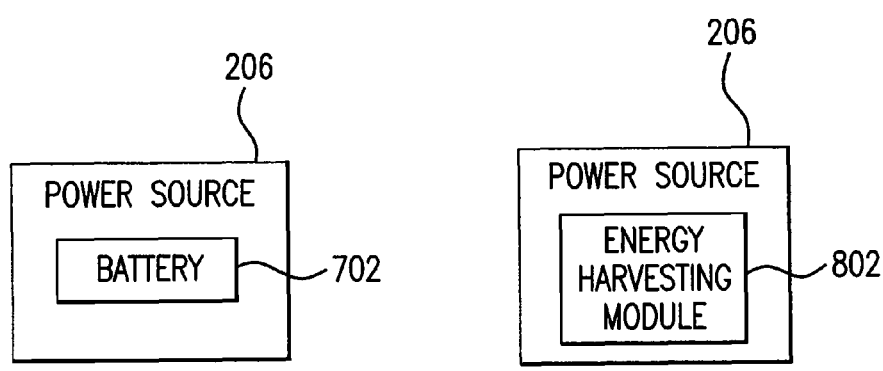
FIG. 7 is a block diagram of a power source according to an embodiment of the present invention.
FIG. 8 is a block diagram of a power source according to another embodiment of the present invention.

Power source 206 may be configured in different ways to provide power to the various elements of ingestible sensor device 104 that require power. For example, as shown in FIG. 7, power source 206 may include a battery 702. Battery 702 is a small battery type that can be contained in housing 208. For example, battery 702 may include a lithium-based cell (e.g., a lithium-thionyl chloride cell, a lithium-manganese dioxide cell, lithium-silver combinations, etc.), alkali-cell, a zinc-air cell, a mercury cell (although these may be undesirable due to safety concerns), a silver-oxide cell, nickel-based cells (e.g., nickel-cadmium), etc. Alternatively, battery 702 may be comprised of biologically safe materials, such as citric juices or semi-solids, whereas juices have the ability to convey acoustic signals simultaneously with chemical reaction providing electrical energy. In some embodiments, where ingestible sensor device 104 passes through the gastrointestinal tract, such as in approximately 24 hours, the energy capacity of battery 702 can be relatively low as compared to other battery-powered devices.

In another embodiment, as shown in FIG. 8, power source 206 may include an energy harvesting module 802. Energy harvesting module 802 harvests, and optionally stores, energy from the environment to provide power. For example, energy harvesting module 802 may be configured as one or more of a variety of types of energy harvesting devices, including a vibratory energy harvesting device, a magnetic energy harvesting device, a heat energy harvesting device, a chemical energy harvesting device, or a mechanical energy harvesting device. For example, in a vibratory energy harvesting embodiment, energy harvesting module 802 may harvest energy due to vibrations of the body of human 102. In an example magnetic energy harvesting embodiment, energy harvesting module 802 may include a magnet-coil combination for energy generation. In an example heat energy harvesting device, energy harvesting module 802 may generate energy from heat of the body of human 102, possibly with reference to an imbedded, insulated source of cold (such as liquid nitrogen).

In a chemical energy harvesting embodiment, energy harvesting module 802 interacts with chemicals of gastrointestinal tract 300 of human 102 to generate energy. For example, energy harvesting module 802 may be configured to interact with acids in gastrointestinal tract 300 (e.g., gastric acids) to create a current that can be used/stored as energy. For instance, in an embodiment, human 102 may ingest an acidic food (solid or liquid), such as a juice containing citric acid (e.g., lemon juice), prior to or at about the same time that a ingestible sensor device 104 is swallowed, to provide an energy source for the ingestible sensor device 104 to harvest.

Energy harvesting module 802 may be configured to store harvested energy in a variety of ways, and may be configured to create a desired voltage from the stored energy in a variety of ways, including in a charge pump configuration (e.g., capacitor-based), using a voltage regulator, etc.

In an embodiment, ingestible sensor device 104 is configured for low power operation, including extreme low power (XLP) operation, enable one or both of a very small battery and energy harvesting to operate ingestible sensor device 104. In an embodiment, circuits of ingestible sensor device 104 are implemented in one or more integrated circuits (ICs), in a technology such as CMOS, or other technology. The IC(s) and any other internal components of ingestible sensor device 104 may be mounted to a circuit board, or mounted directly to housing 208. Thus, in embodiments, power source 206 is configured for low power output, including supplying power in the milli-Watt and micro-Watt ranges. Such low power requirements enable a small power source 206.

In a CMOS embodiment, MOSFET circuits may be configured to operate in a deep sub-threshold voltage (sub-Vt) mode, which lowers their switching time to acoustic switching frequencies, and lowers their power consumption by orders of magnitude. In such a mode the MOSFET devices operate as analog devices. Such operation was demonstrated in the mid-1980's by Carver Meade with regard to eye and ear chips. Such a mode of operation eliminates the need for digitizing the sensor information, which can be very power intensive, and which further reduces the power consumption by a large factor. Further details on such sub-threshold voltage MOSFET circuits may be found in the following U.S. Patents, which are incorporated herein by reference in their entirety: U.S. Pat. Nos. 6,198,324, 6,252,448, 6,297,668, and 6,333,656.

Figure 9:
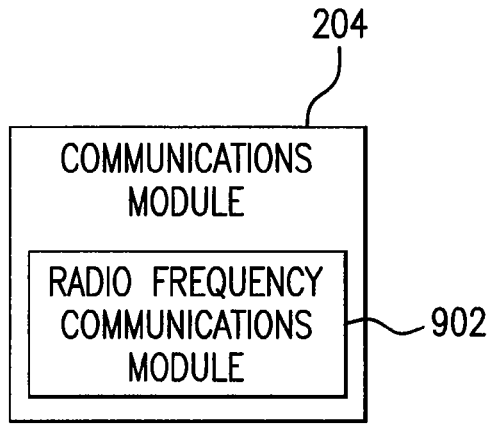
FIG. 9 is a block diagram of a communications module according to an embodiment of the present invention.

Communications module 204 may be configured in various ways to communicate with computing device 108, including transmitting signals (e.g., communication signal 106) to computing device 108 and/or receiving signals from computing device 108. For example, in an embodiment as shown in FIG. 9, communications module 204 includes a radio frequency (RF) communications module 902, which includes a RF transmitter circuit. In an embodiment, the transmitter circuit may generate communication signal 106 to include information modulated on a carrier signal having a radio frequency. The transmitter circuit may be mixer based, switch/transistor based, or include other type of up-converter and/or modulator circuit. RF communications module 902 may modulate sensor output signal 202 onto the RF carrier signal to generate communication signal 106. Communication signal 106 may be radiated from radiating element 602 coupled to communications module 204, which may be a suitable type of antenna mountable in or on ingestible sensor device 104, including forming all or a portion of housing 208 itself.

In an embodiment, RF communications module 902 may further include a receiver circuit for receiving a communication signal from computing device 108. Thus, for example, RF communications module 902 may include a down-converter and/or demodulator circuit. In such an embodiment, RF communications module 902 may include any suitable type of RF communications receiver device, including a heterodyne (e.g., superheterodyne) receiver circuit, and may include a mixer circuit, such as a diode-based mixer, a switch/transistor based mixer, etc. Radiating element 602 may receive the communication signal from computing device 108, and pass the received communication signal to RF communications module 902 for demodulation/down-conversion. Other electromagnetic embodiments, such as optical communication, may also be used.

Figure 10:
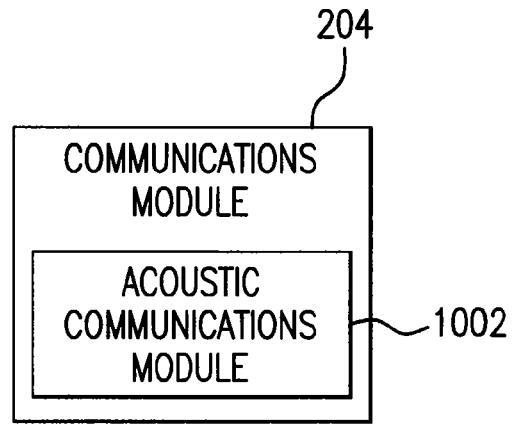
FIG. 10 is a block diagram of a communications module according to another embodiment of the present invention.

However, RF communication is disadvantageous because of high power usage, which requires a large battery. Inclusion of a large battery in an ingestible device such as ingestible sensor device 104 increases the size of ingestible sensor device 104, making it difficult to swallow and increasing the danger that it will become trapped in the digestive tract. Therefore, a lower-power solution is needed. As shown in FIG. 10, an example low-power communications module 204 may include an acoustic communications module 1002, configured to transmit and/or receive a communications signal in an acoustic manner. For example, acoustic communications module 1002 may include an acoustic transducer or multiple acoustic transducers. Sensor output signal 210 is modulated on an acoustic signal that is transmitted as communications signal 106 by the acoustic transducer(s). The acoustic communications signal 106 may be transmitted by the radiating element, which may be an acoustic transducer or "speaker"-type element that vibrates at acoustic frequencies. An example acoustic frequency range in which acoustic communication signal 106 may be transmitted is 20 Hz to 16 KHz, although the frequency may be an acoustic frequency higher or lower than this range in some applications. An example frequency for acoustic communications signal 106 is 40 Hz. Acoustic pressures according to embodiments may have various levels, including greater or lower than 1 Pa, including in the KPa (or greater) range to the µPa (or less) range.

Figure 11:
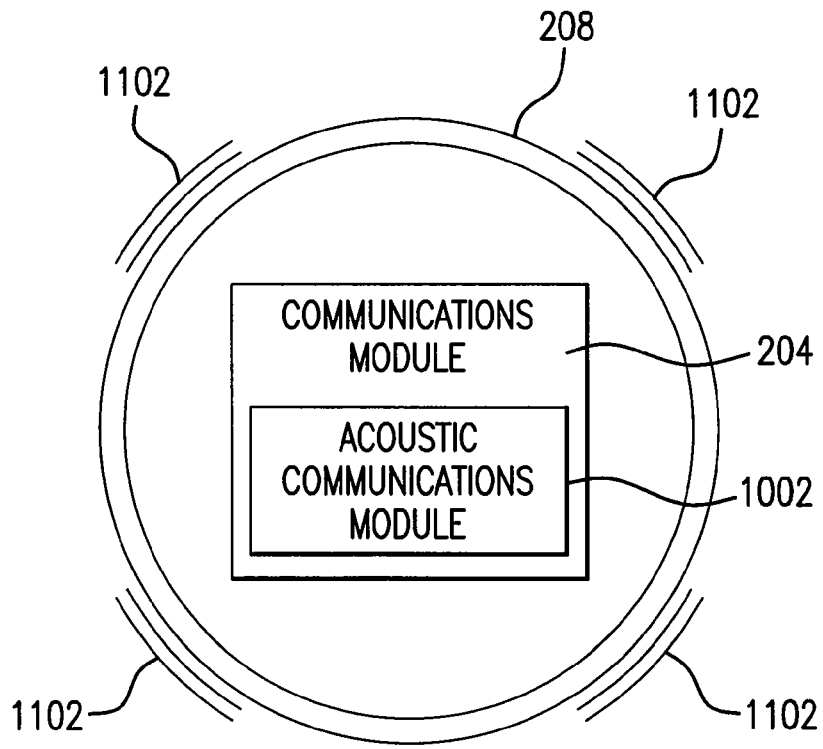
FIG. 11 is a block diagram of an ingestible capsule according to another embodiment of the present invention.

For example, FIG. 11 shows a view of ingestible sensor device 104, with communications module 204 including acoustic communications module 1002. In FIG. 11, communications module 204 is coupled to housing 208. Housing 208 vibrates according to acoustic communications module 1002 to transmit a communications signal 1102, which is an acoustic version of communications signal 106. Thus, in FIG. 11, housing 208 functions as an acoustic radiating element, vibrating at acoustic frequencies according to acoustic communications module 1002.

In a likewise fashion, communications module 204 may include an ultrasonic communications module 1002, configured to transmit and/or receive a communications signal at ultrasonic frequencies (e.g., greater than 20 KHz). Generally, transducers are smaller for ultrasonic frequencies, which is useful for a very small sensor device. However, smaller devices also generally transmit less power through a medium and thus need to have a high power input and hence a larger battery. Higher frequency transducers do generally have a higher bandwidth and may have an impact on the amount of sensor data can be transmitted to a receiver. However, higher frequencies are attenuated faster as the signal propagates through the acoustic medium, and requires a higher transmit power to compensate. A person skilled in the art of acoustic transducers will be able to select an appropriate frequency range for an ideal situation of size and power consumption.

As shown in FIG. 11, housing 208 may be spherical in shape. Alternatively, housing 208 may be capsule shaped, or may have some other shape. A spherical shape for housing 208 enables transmission of acoustic communication signal 1102 in a substantially uniform manner in all directions. When multiple receiving sensor links 2002 and/or computing devices 108 are used, it is likely that each sensor link 2002 and/or computing device 108 will appear in a different orientation with respect to ingestible sensor device 104. A uniform transmission is desired to reduce the effects substantially less power being radiated in a particular direction. In an alternative embodiment to the spherical embodiment, multiple transducers activated in a non-overlapping time sequence may provide an equivalent power scenario available to sensor link modules 2002 and/or computing devices 108 over multiple attempts with different orientations of more directional transducers, such as with peak transmission orientations at right angles to each other.

Figure 12:
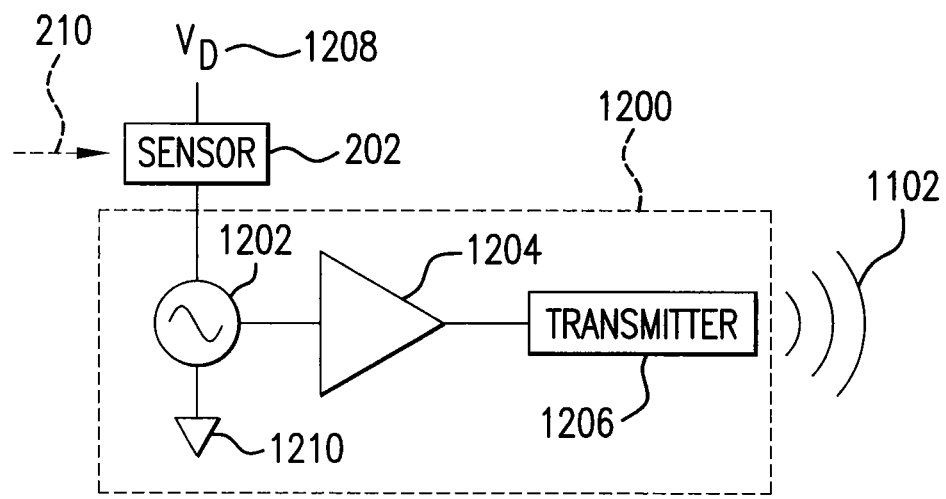
FIG. 12 is a circuit diagram of an acoustic communications module according to an embodiment of the present invention.

FIG. 12 shows an example circuit 1200 for acoustic communications module 1002, according to an embodiment of the present invention. As shown in FIG. 12, circuit 1200 includes an oscillator 1202, an amplifier 1204, and an acoustic transmitter 1206. In the example of FIG. 12, sensor 202 has a resistance (or other impedance value) that changes based on the sensed stimulus, stimulus 210. For example, sensor 202 may be a temperature sensor. Sensor 202 is coupled in series with a current-dependent oscillator 1202, which may be configured to operate in a deep-threshold voltage (Vt) range to lower an oscillation frequency generated by oscillator 1202 to a desired acoustic frequency range. As the resistance of sensor 202 changes, the oscillator frequency changes in a predictable way. An output of oscillator 1202 is coupled to an input of an amplifier circuit 1204 for amplification. An output of amplifier 1204 is input to acoustic transmitter 1206 (which may include or be coupled to an acoustic radiating element 602), such as an acoustic actuator or transducer, that acts as a "speaker" to send the acoustic data out on acoustic communication signal 1102. For example, as described above with respect to FIG. 11, housing 208 may be coupled to the output of acoustic transmitter 1206 to increase an acoustic transmission surface area. In an embodiment, sensor 202 is digitized, and acoustic communication signal 1102 output by acoustic transmitter 1206 is a digital signal. Use of a digital signal can increase robustness against error in the communications path.

In an embodiment of FIG. 12, multiple sensors 202 may be used to significantly enhance the function of sensor device 104. Multiple temperature sensors 202 offer robustness in redundant operation, mitigating a loss or malfunction of one sensor. Additionally, multiple operational sensors 202 offer a potential to evaluate differentials between sensors 202. Use of normalized sensor readings from differences between multiple sensors 202 can be used, for example, to remove a background daily core body temperature fluctuation from impacting localized hot spot evaluation.

In a simplistic embodiment, multiple sensors 202 can be configured to be connected serially in time (that is, time division multiplexed) to oscillator 1202, amplifier 1204, and transmitter 1206. In a more mechanically complex implementation, a single sensor 202 can be mechanically manipulated or directed to observe an entire environment surrounding sensor device 104.

An example of a simple implementation of a multiple sensor 202 temperature device 104 includes two or more thermister-equivalent devices on opposing sides or (in the case of more than two) reasonably equally divided radians on the exterior of ingestible sensor device 104. In this example, ingestible sensor device 104 is able to collect a more localized temperature reading. A higher temperature reading on a small subset of sensors 202 likely indicates a higher localized cellular activity, such as in the case of an infection, an allergic reaction to a substance, or developing cancer material. Furthermore, an example of a mechanically advanced embodiment includes a highly directional temperature sensor 202, such as an infrared (IR) detection device, and either a mechanical means to revolve the IR detection device or a mechanical means to revolve the detection range, such as a spinning mirror. In such an advanced embodiment, sensor 202 (an IR detector, for example) may continuously modulate its output. This causes a continuous modulation of oscillator 1202 at a given frequency, and a continuous modulation of transmission 1102 can occur. In this embodiment, an analog transmission 1102 may provide a detailed scan of thermal activity along an entire gastrointestinal tract 300.

Communications module 204 may be configured to modulate information of sensor output signal 212 according to a variety of modulation techniques, including amplitude modulation (AM), frequency modulation (FM), and phase modulation (PM), and including any combination of these modulation techniques, including in quadrature modulation schemes or any other modulation techniques. Example modulation techniques that may be used are described in the following co-pending U.S. Patent Applications, each of which is incorporated by reference herein in its entirety: U.S. patent application Ser. No. 11/851,236, titled "System and Method for Acoustic Data Transmission;" and U.S. patent application Ser. No. 11/896,946, titled "Methods and Systems for Acoustic Data Transmission;" and U.S. patent application Ser. No. 11/851,214, titled "System and Method for Acoustic Information Exchange Involving an Ingestible Low Power Capsule."

In an embodiment, ingestible sensor device 104 stores an identification number, which may be unique for each ingestible sensor device 104. The identification number may be unique worldwide or merely in a particular locality, or even just in a particular batch of ingestible sensor devices 104. The identification number may be a sequence of bits, such as 8 bits, 16 bits, 32 bits, etc. The identification number or a subset thereof may be used to identify the product type of ingestible sensor device 104 and/or the type(s) of sensor 202 or available functions on the particular ingestible sensor device 104. Furthermore, the identification number can be used to track whether human 102 has actually swallowed ingestible sensor device 104, whether the correct ingestible sensor device 104 was swallowed, and can thus help monitor whether human 102 is following a proper procedure for using ingestible sensor device(s) 104. Such information can be displayed on computing device 108, and may be provided to remote entity 404.

For example, in an embodiment, FM may be used to send the output information sensor 202 from ingestible sensor device 104, in a variety of schemes. For instance, an example FM protocol that can handle multiple sensors 202a-202c is described below:

$F_{Drone}$=a drone frequency,
$F_0$=a frequency for bit zero,
$F_1$=a frequency for bit 1,
$F_i$=a data frequency, where i=a, b, c, etc for sensors 202a-202c, respectively, and
$F_{ID}$=a frequency sequence of zero bits ($F_0$) and one bits ($F_1$) for the identification number of the particular ingestible sensor device 104.

The drone frequency $F_{Drone}$ is used to provide a detectable separation between frequencies Fa, Fb, and Fc related to data of sensors 202a-202c. The presence of drone frequency $F_{Drone}$ may not be required in all implementations. Frequencies Fa, Fb, and Fc have frequency ranges that are non-overlapping so that communications related to sensors 202a-202c can be distinguished from each other. In an embodiment, after a ingestible sensor device 104 is swallowed, the swallowed ingestible sensor device 104 is configured to serially send out the following frequency sequence:

$F_{Drone} F_{ID} F_{Drone} F_a F_{Drone} F_b F_{Drone} F_c F_{Drone} F_{ID} F_{Drone}$ Thus, in a first time slot ($F_{Drone}$), ingestible sensor device 104 transmits the drone frequency $F_{Drone}$. In a second time slot ($F_{ID}$), ingestible sensor device 104 transmits the identification number for the particular ingestible sensor device 104 as a series of 0 and 1 bits, respectively represented by frequencies $F_0$ and $F_1$. In a third time slot ($F_{Drone}$), ingestible sensor device 104 transmits the drone frequency $F_{Drone}$. In a fourth time slot ($F_a$), ingestible sensor device 104 transmits information related to sensor 202a. The information is transmitted at a central frequency of $F_a$ that varies in frequency in a manner according to information of sensor output signal 212a. Thus, information of sensor 202a is transmitted in the fourth time slot. In a fifth time slot ($F_{Drone}$), ingestible sensor device 104 transmits the drone frequency $F_{Drone}$. In a sixth time slot ($F_b$), ingestible sensor device 104 transmits information related to sensor 202b. The information is transmitted at a central frequency of $F_b$ that varies in frequency in a manner according to information of sensor output signal 212b. Thus, information of sensor 202b is transmitted in the sixth time slot. In a seventh time slot ($F_{Drone}$), ingestible sensor device 104 transmits the drone frequency $F_{Drone}$. In an eighth time slot ($F_c$), ingestible sensor device 104 transmits information related to sensor 202c. The information is transmitted at a central frequency of $F_c$ that varies in frequency in a manner according to information of sensor output signal 212c. Thus, information of sensor 202c is transmitted in the eighth time slot. In a ninth time slot ($F_{Drone}$), ingestible sensor device 104 transmits the drone frequency $F_{Drone}$. In a tenth time slot ($F_{ID}$), ingestible sensor device 104 transmits the identification number for the particular ingestible sensor device 104. In a third time slot ($F_{Drone}$), ingestible sensor device 104 transmits the drone frequency $F_{Drone}$. In subsequent time slots, information related to sensors 202a-202c can be further transmitted at frequencies $F_a$-$F_c$, and the identification number $F_{ID}$, can be further transmitted, separated by the drone frequency FD as desired.

Computing device 108 may receive this frequency sequence, and due to the ordering of frequency signals, and the different frequencies used, can store the received information of sensors 202a-202c in an organized manner.

In alternative embodiments, utilization of phase encoding of data in place of the previously detailed frequency encoding may be more beneficial to either overall frequency use and/or time necessary to transmit desired information. Furthermore, a combination of phase encoding and frequency encoding is realized as a very efficient means for information transmission and a desired embodiment of the present invention.

In such embodiments, information from any number of sensors 202 can be accommodated. In some embodiments, the drone frequency FD may not be necessary. Furthermore, in some embodiments, the identification number sequence, $F_{ID}$, may not be necessary (e.g., if identical ingestible sensor devices 104 are individually used by human 102). Any length for of identification number may be used.

A time interval, $T_d$, may be used for each of the time slots described above. The time interval $T_d$ may be bounded by a minimum time interval for $T_d$, $T_{dmin}$, and a maximum time interval for $T_d$, $T_{dmax}$. The minimum time interval, $T_{dmin}$, may be determined by noise issues. The maximum time interval, $T_{dmax}$, may be determined by power consumption issues (such as a charge lifespan of battery 702) of ingestible sensor device 104. Furthermore, a duty cycle, $T_c$, may be used for the time slots described above. The duty cycle, $T_c$, may be bounded by a minimum duty cycle length, $T_{cmin}$, and a maximum duty cycle length, $T_{cmax}$. The minimum duty cycle, $T_{cmin}$, may be determined by requirements of the particular diagnostic test(s) to be performed by ingestible sensor device 104, and the maximum duty cycle, $T_{cmax}$, may be determined by power consumption issues (such as a charge lifespan of battery 702) of ingestible sensor device 104.

Figure 13:
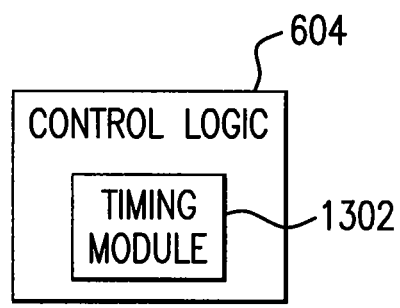
FIG. 13 is a block diagram of a control logic according to an embodiment of the present invention.

Control logic 604 shown in FIG. 6, when present, may be configured in a variety of ways. Control logic 604 can be configured to enable or disable operation of sensor 202 and/or communications module 204 at various times during the transit of ingestible sensor device 104 through gastrointestinal tract 300. This may be done to save power for ingestible sensor device 104, for example. Control logic 604 may enable or disable operation of elements of ingestible sensor device 104 based on time and/or location of ingestible sensor device 104. For example, FIG. 13 shows control logic 604 including a timing module 1302. Timing module 1302 may be used to enable and disable sensor 202 and/or communication module 204 in a periodic manner or at predetermined time intervals, to transmit sensor data at set periodic time intervals as ingestible sensor device 104 transits through gastrointestinal tract 300. For example, timing module 1302 may be configured to gate power from power source 206 to sensor 202 and/or communications module 204, or to gate them in other manners to enable or inhibit their operation as desired. Alternatively, control logic 604 may receive data from sensor(s) 202 to determine a relative location of ingestible sensor device 104 in gastrointestinal tract 300. Based on the determined location, control logic 604 may enable or disable operation of ingestible sensor device 104.

Operation of ingestible sensor device 104 may be gated and controlled by control logic 604, which itself may be operating in a sub-threshold voltage (Vt) manner (e.g., to save power), or control logic 604 may operate in normal bias modes. In an embodiment, ingestible sensor device 104 is an autonomous device with one way communication (transmission capability), so that control logic 604 may be extremely simple, and thus would not consume much power even when operating in normal bias modes. However, in other embodiments, ingestible sensor device 104 may communicate in both directions, and may be configured to receive instructions from computing device 108, and thus control logic 604 may have additional complexity in order to decode and implement received instructions, and for other reasons.

Figure 14:
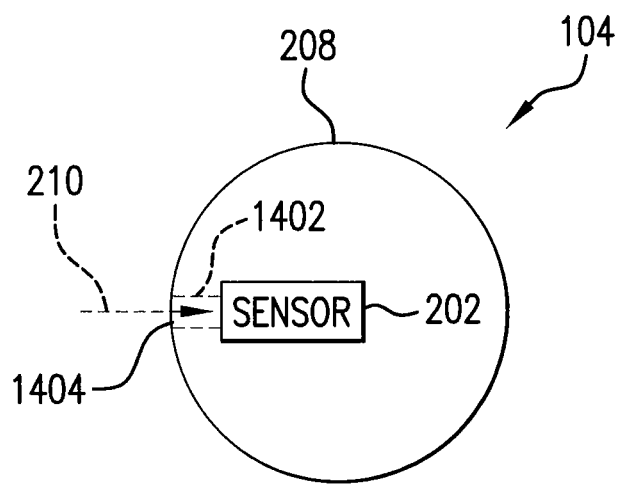
FIG. 14 is a block diagram of an ingestible capsule according to another embodiment of the present invention.

Ingestible sensor device 104 can be configured in a variety of ways to enable sensor 202 to receive stimulus 210. For example, as shown in FIG. 14, housing 208 of ingestible sensor device 104 may have one or more ports 1402 for receiving a material (e.g., bodily chemical, including a bodily fluid, tissue, etc.) of gastrointestinal tract 300, to be received and sensed by sensor 202. Port 1402 may have a round or other shaped opening 1404 at a surface of housing 208. Port 1402 may be open or may have a filter material residing therein. Sensor elements, for example electrochemical electrodes with or without bio-recognition elements such as enzymes, may be patterned directly on the surface of the swallowable sensor device. A polymer coating may protect the sensor element, may provide added functionality (e.g., by increasing the conductivity between electrode and a bio-recognition element or respond to changes in chemical environment, such as pH), and may eliminate chemical interferences. Such a polymer or other filter material (e.g., a grating, a porous material, etc.) may be used to block undesired material of gastrointestinal tract 300 while enabling a desired material to reach sensor 1402.

Figures 15, 16:
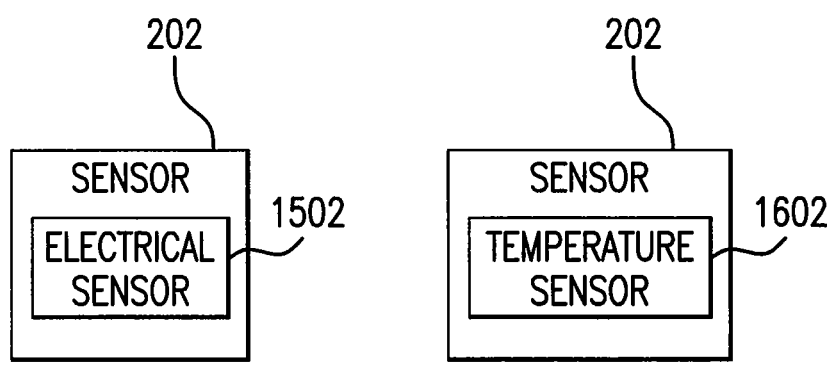
FIG. 15 is a block diagram of a sensor according to an embodiment of the present invention.
FIG. 16 is a block diagram of a sensor according to another embodiment of the present invention.

As described above, sensor 202 can be configured in a variety of ways to sense a wide variety of conditions of human 102. For example, as shown in FIG. 15, sensor 202 comprises an electrical sensor 1502. Electrical sensor 1502 may be coupled to a power and ground signal (e.g., power 1208 and ground 1210 shown in FIG. 12), and may vary in impedance (e.g., resistance, capacitance, inductance) in relation to stimulus 210. For example, electrical sensor 1502 may be a temperature sensor 1602, as shown in FIG. 16. In such an embodiment, a resistance of temperature sensor 1602 may vary with temperature (such as described above with respect to FIG. 12), to generate a sensor output signal 1210 that indicates temperature. Alternatively, temperature sensor 1602 may be configured in other ways.

Figure 17:
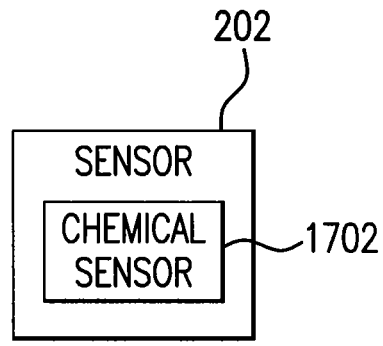
FIG. 17 is a block diagram of a sensor according to another embodiment of the present invention.
Figure 18:
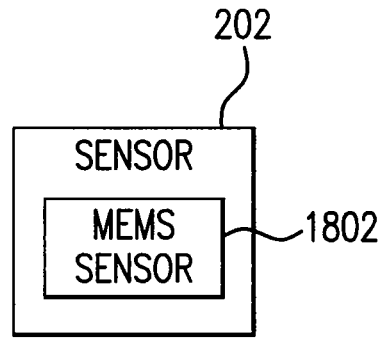
FIG. 18 is a block diagram of a sensor according to another embodiment of the present invention.
Figure 19:
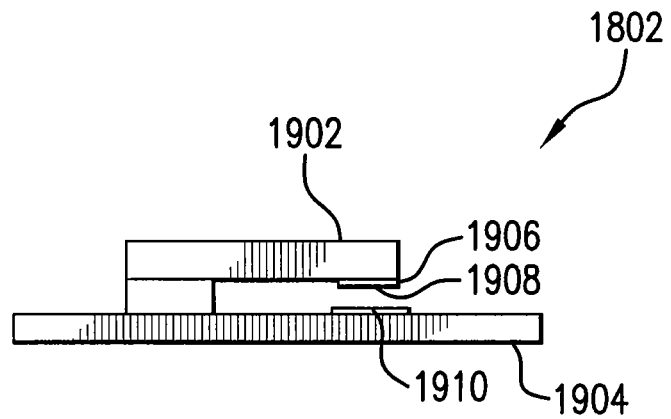
FIG. 19 is a block diagram of a sensor according to another embodiment of the present invention.

In another embodiment, sensor 202 may comprise a chemical sensor 1702, as shown in FIG. 17. Chemical sensor 1702 may be configured to detect the presence of a particular chemical or a chemical family in gastrointestinal tract 300. For example, chemical sensor 1702 may be a micro-electromechanical system (MEMS) sensor 1802, as shown in FIG. 18. MEMS sensor 1802 can be configured in a variety of ways to detect chemicals. For example, MEMS sensor 1802 may include a MEMS cantilever 1902 on a substrate 1904, as shown in FIG. 19. FIG. 19 shows a cross-sectional view of a MEMS cantilever 1902. In an embodiment, MEMS cantilever 1902 is an oscillating cantilever, configured to oscillate in a selected acoustic frequency range. Cantilever 1902 may be coated with a material configured to capture molecules of a chemical to be sensed. On capture, a frequency of oscillation of cantilever 1902 would change, indicating that the chemical is sensed.

In another embodiment, MEMS sensor 1802 may include a surface acoustic wave (SAW) sensor. The SAW sensor may be coated with a material configured to react with molecules to be sensed. On capture, the increased mass loading on the surface of the SAW sensor results in a change in an electrical property of the SAW sensor (most often the resonant frequency) indicating that a chemical is sensed.

Figure 28:
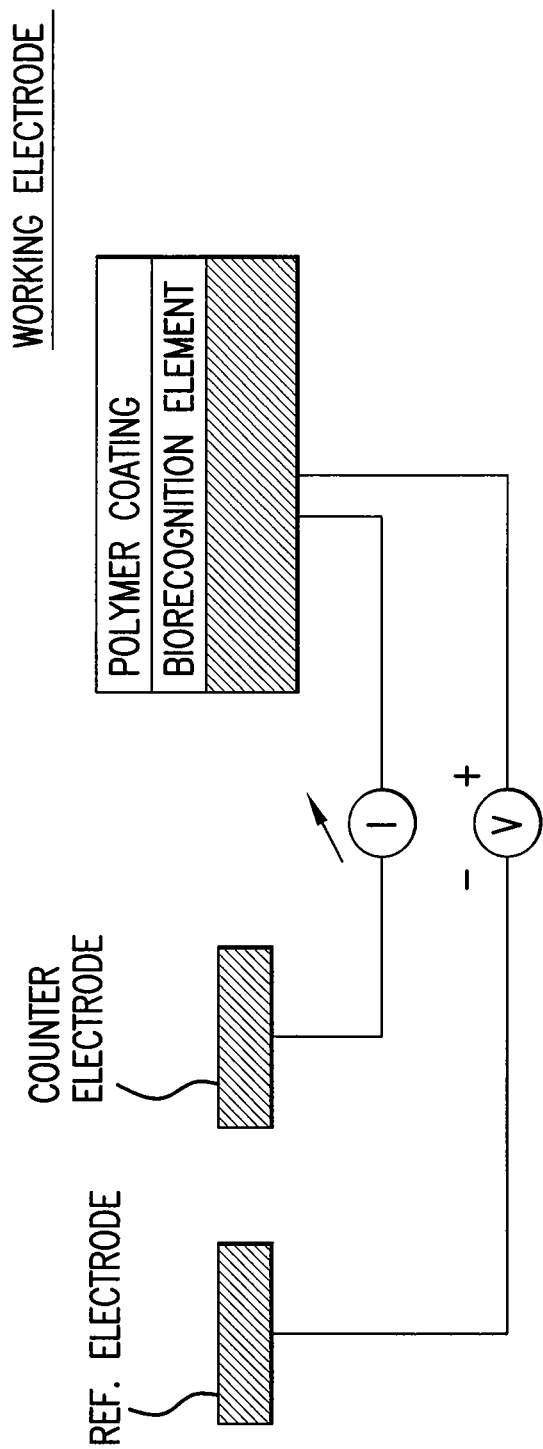
FIG. 28 is a block diagram of an electrochemical sensor according to an embodiment of the present invention.

In another embodiment, chemical sensor 1702 may be an electrochemical sensor as shown in FIG. 28. The electrochemical sensor may be a three electrode cell in which the working electrode is coated with a material configured to react with molecules to be sensed. The reaction occurring at the surface of the working electrode leads to a change in oxidation state, which is manifested as a flow of current into or out of the electrode, indicating that the chemical is sensed.

In another embodiment, chemical sensor 1702 may be an optical sensor. The optical sensor may be coated with a material configured to react with molecules to be sensed and change its optical properties as a result. For example, an optical coating may be utilized that fluoresces when a particular chemical of interest reacts with it. Alternatively, the chemical reaction of interest could cause a reduction in the natural fluorescence of the coating.

In another embodiment, cantilever 1902 may be used as vibration sensor or pressure sensor. For example, when cantilever 1902 is vibrated, or when sufficient pressure is applied to cantilever 1902, end 1906 of cantilever 1902 may make contact with substrate 1904 to activate MEMS sensor 1802. For instance, a contact area 1908 on end 1906 of cantilever 1902 may be an electrically conductive material that makes electrical contact with a contact area 1910 on substrate 1904 when cantilever 1902 bends, to create an electrical current path, thereby allowing cantilever 1902 to operate as a switch. Cantilever 1902 can be formed in a variety of ways, including standard photolithography and other MEMS fabrication techniques.

In another embodiment, sensor 202 may be a blood sensor. The presence of blood in the gastrointestinal tract can indicate a medical condition such as cancer or pre-cancerous polyps. Existing chemical tests for occult gastrointestinal tract blood are carried out on stool samples. Such tests are based on the pseudo-peroxidase activity of heme, which causes a breakdown of hydrogen peroxide that can then be detected through the use of a color-changing dye or marker. This and similar methods are not suitable for use in-vivo due to the reliance on intermediate reagents and the observation of a color change.

Figure 29A:
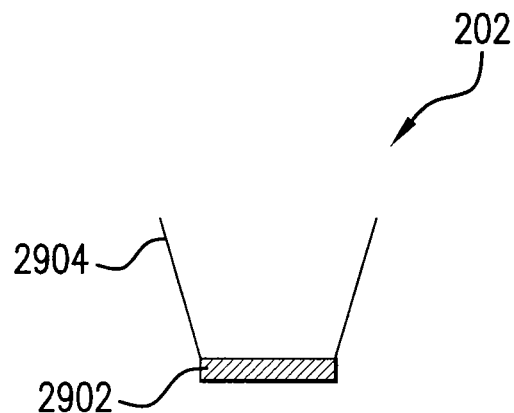
FIG. 29A is a block diagram of an enzyme sensor according to an embodiment of the present invention.

For in-vivo use, such as on ingestible sensor device 104, an enzyme biosensor may be used to detect the presence of blood. An enzyme, for example heme oxygenase, that reacts specifically with heme or another factor in the blood, may be fixed to a metal microelectrode. FIG. 29A illustrates an example sensor 202, wherein sensor 202 is configured to detect blood. In this example, sensor 202 includes an enzyme 2902 coupled to a metal electrode 2904. Enzyme 2902 may be exposed to the gastrointestinal tract to detect one or more substrates present in the gastrointestinal tract. Although the present example will be described with respect to the use of heme oxygenase as an enzyme to detect heme in the blood, one of skill in the art will recognize that other enzymes may be used in a similar manner to detect other substrates indicative of the presence of blood.

Figure 29B:
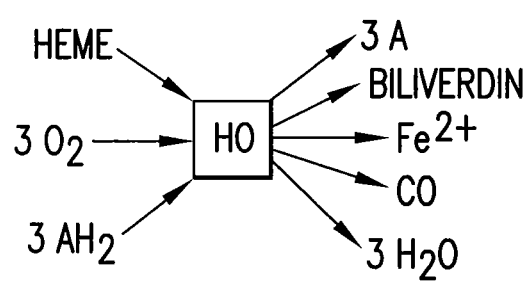
FIG. 29B is a diagram of an exemplary chemical reaction in an enzyme sensor according to an embodiment of the present invention.

FIG. 29B illustrates the oxidation reaction catalyzed by heme oxygenase (HO). Specifically, the following reaction occurs:

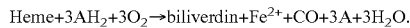

Heme+$3AH_2$+$3O_2$→biliverdin+$Fe^{2+}$+CO+3A+$3H_2O$.

When HO is present, a reaction between heme, ascorbic acid, and oxygen (the reactants) is instigated. By-products of this oxidation reaction include, among other things, bilirubin and carbon monoxide. This forward reaction can be detected in multiple ways.

In an embodiment, the oxidation reaction is detected through direct electron transfer. In this embodiment, enzyme 2902 includes heme oxygenase, which is coupled to metal electrode 2904. During oxidation, an electron is produced. This electron is transferred from the reaction site into electrode 2904, causing a change in current. This current change can be monitored using, for example, a high impedance amplifier.

The direct electron transfer embodiment presumes that the electron will flow from the reaction site to the electrode with fairly low impedance. In another embodiment, the reaction can be detected by monitoring the concentration of reactant and/or by-product at the reaction site. A reduction in a reactant (such as oxygen) or an increase in a by-product (such as carbon monoxide) is indicative of the reaction and can be measured with electrochemical or other methods. For example, measurement may occur using amperometric detection. With amperometric detection, a generated current is proportional to a detected level of a particular substance. In this example, an amperometric detector may detect a change in the level of carbon monoxide, such that a current change due to an increase in carbon monoxide is indicative of the reaction. Similarly, an amperometric detector may detect a change in the level of oxygen, such that a current change due to a decrease in oxygen is indicative of the reaction.

Such a binary (that is, blood or no blood) determination as to whether blood exists in the gastrointestinal tract is autonomous, in that it eliminates the need for interpretation and/or intervention from experts to make the determination. Such a sensor also allows the measurement to be made remotely, with the result of the measurement transmitted acoustically to a receiver.

Additionally, an approximate level of blood in the gastrointestinal tract can be determined. In an embodiment where direct electron transfer is used to detect heme, the level of current produced by the electron transfer is a function of the oxidation rate, which in turn is indicative of the level of blood present. Similarly, in an embodiment where amperometric detection is used to detect changes in the level of reactants and/or by-products, the amount of reactant and/or by-product can be determined from the current generated.

Sensors 202 incorporated into ingestible sensor device 104 may be configured to be specific to a diagnostic test prescribed by a physician of human 102. For example, temperature sensor 1602 may be imbedded in an integrated circuit of ingestible sensor device 104 to monitor a core body temperature and provide a temperature reference for other sensor data. Others of sensors 202 may be configured to detect the presence of blood to locate sources of bleeding in gastrointestinal tract 300. Sensors 202 may be configured to analyze enzymes and digestive fluids for the presence of chemical "markers" for specific diseases, including cancer. An array of sensors 202 may be used for a broad spectrum of tests for general health, or focus on a specific disease. A physician may first prescribe a ingestible sensor device 104 configured for diagnosing general health of human 102. Based on the results of the analysis of data received from the ingestible sensor device 104, the physician may prescribe a second ingestible sensor device 104 configured to diagnose a specific disease or other suspected problem.

In embodiments, sensors 202 can be configured to detect various further conditions, including detecting a heartbeat, breathing, a pH level, and other materials, chemicals, and enzymes in gastrointestinal tract 300 that are relevant to patient health, including blood sugar, ulcers, tumors, cancer pre-cursers, etc.

Figure 20:
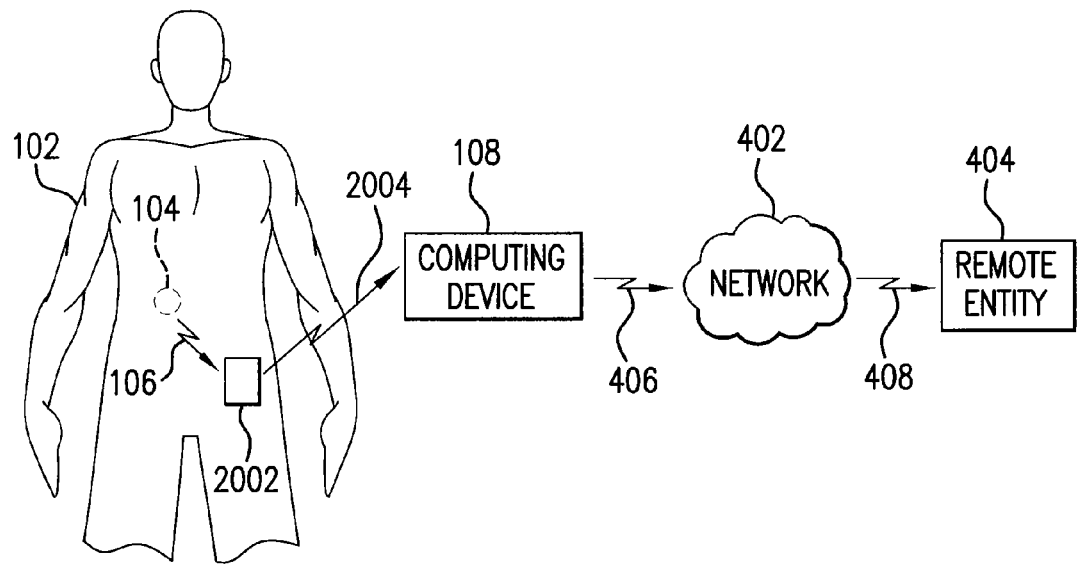
FIG. 20 is a block diagram of an exemplary communications network utilizing a sensor link module according to an embodiment of the present invention.

As described above, ingestible sensor device 104 communicates with computing device 108. Computing device 108 may be configured to communicate with ingestible sensor device 104 in a variety of ways. For example, as shown in FIG. 1, ingestible sensor device 104 may communicate directly to computing device 108. Alternatively, ingestible sensor device 104 may communicate with computing device 108 via an intermediate sensor link module 2002, as shown in FIG. 20. Sensor link module 2002 receives communication signal 106 from sensor 202. Sensor link module 2002 transmits a communication signal 2004 to computing device 108, to provide the information sensed by sensor 202 to computing device 108. For example, sensor link module 2002 may be used when ingestible sensor device 104 communicates with an acoustic communications signal or with a RF communication signal having a power level to low to reliably be received by computing device 108. As shown in FIG. 20, sensor link module 2002 is coupled to human 102.

Multiple sensor link modules 2002 may comprise a system as an alternative embodiment to FIG. 20. The present invention includes in this embodiment a capability of location detection through triangulation and other algorithms, capable of detecting sensor device 104 to a very accurate, three-dimensional location within human 102. Sensor readings from ingestible sensor device 104 in combination with accurate location information taken at the time sensor device 104 detects a condition, material, or attribute may provide a very valuable tool for surgeons eliminating some or all exploratory surgical time and complications (infections and incision size, etc) in identifying an area of operation, or providing a much more reduced area of treatment for a number of cancers.

Additionally, a sensor device 104 with accurate location tracking capability of sensor link modules 2002 may provide a doctor with information as to what additional procedures are best to evaluate a further procedure. For example, a location indication may be used to make a choice whether an endoscope (for the stomach), a double balloon endoscope (for the small bowell), or colonoscopy (for the large intestine) should be used to further investigate an area of interest made available by sensor readings.

Figure 21:
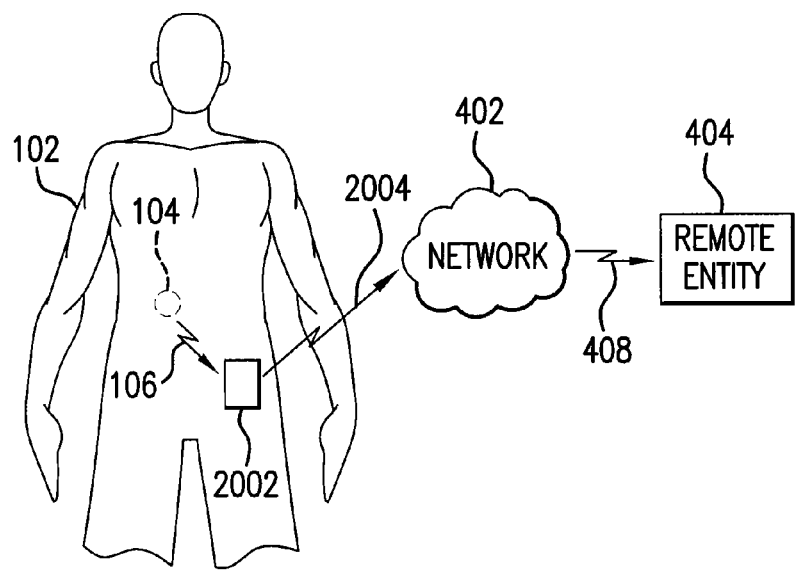
FIG. 21 is a block diagram of an exemplary communications network utilizing a sensor link module according to another embodiment of the present invention.

In another embodiment, as shown in FIG. 21, sensor link module 2002 may provide a communication interface between ingestible sensor device 104 and network 402, such that a separate computing device 108 is not required. In such an embodiment, sensor link module 2002 may perform some or all functions of computing device 108 described above, and thus sensor link module 2002 may be referred to as a computing and/or storage device.

Figure 22:
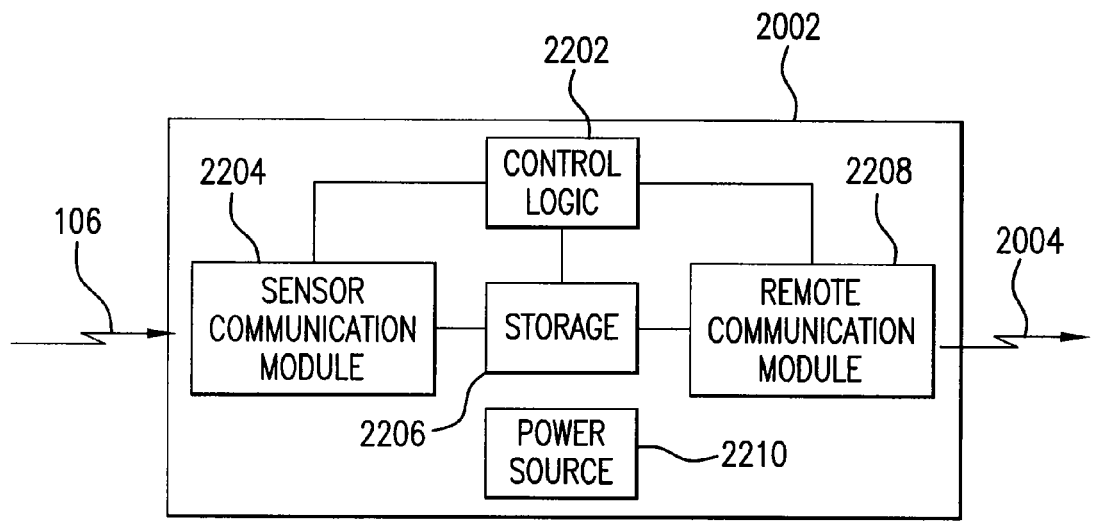
FIG. 22 is a block diagram of a sensor link module according to an embodiment of the present invention.

In embodiments, sensor link module 2002 may be configured in various ways. For instance, FIG. 22 shows an example sensor link module 2002, according to an example embodiment of the present invention. As shown in FIG. 22, sensor link module 2002 includes a control logic 2202, a sensor communication module 2204, a storage 2206, a remote communication module 2208, and a power source 2210. In an embodiment where sensor link module 2002 is acting as a pure storage device, remote communication module 2208 is optional.

Sensor communication module 2204 receives communication signal 106 from ingestible sensor device 104. Thus, in embodiments, sensor communication module 2204 may be configured to receive an RF version and/or an acoustic version of communication signal 106. Sensor communication module 2204 demodulates the sensor related information/data of communication signal 106. Furthermore, sensor communication module 2204 may process and/or convert a format of the information received in communication signal 106. For example, sensor communication module 2204 may perform an analog-to-digital (A/D) conversion of the received sensor data, and outputs a sensor data signal. Additionally or alternatively, sensor communication module 2204 may normalize data, convert a relative data to an absolute value, and/or apply a compression algorithm to the outbound data stream. The sensor data signal may be received by storage 2206 and/or by control logic 2202. In an embodiment, sensor link module 2002 may convert communication signal 106 (for example, an acoustic protocol) into an industry adopted or standardized communication protocol. Example industry adopted protocols include, for example and without limitation, a Medical Implant Communications Services (MICS) protocol and RF medical devices standardized protocol. Such an embodiment may not require much storage 2206, potentially as small as a single register device.

In other embodiments, storage 2206 is configured to store the sensor data of the sensor data signal. Storage 2206 may include any type of suitable storage, including a hard drive and/or imbedded or detachable memory devices. For example, in an embodiment, storage 2206 includes a read/write non-volatile memory such as a secure digital (SD) memory card as is typically used in PDAs and digital cameras. Storage 2206 can output the stored data in a stored sensor data signal, for subsequent transmission to computing device 108 by remote communication module 2208. In an embodiment, storage 2206 is removable such as, for example, SD memory. In such an embodiment, physical removal of the memory and insertion into computing device 108 or remote entity 404 is both possible and effective.

Control logic 2202 is configured to control operation of sensor link module 2002.

Remote communication module 2208 receives the stored sensor data signal, and formats the sensor-related data for transmission. Furthermore, remote communication module 2208 transmits the sensor data in communication signal 2004. Remote communication module 2208 may be configured to transmit communication signal 2004 in a variety of formats/protocols, such as a standard RF communication protocol including Bluetooth, IEEE 802.11, Zigbee, or other communication protocol, standard or otherwise. For example, in embodiments, computing device 108 may be a Bluetooth, 802.11, and/or Zigbee configured handheld device such as cell phone, personal digital assistant (PDA), a Blackberry™, wrist watch, music player, or laptop, or other type of computer, handheld, desktop, or otherwise.

Figure 23:
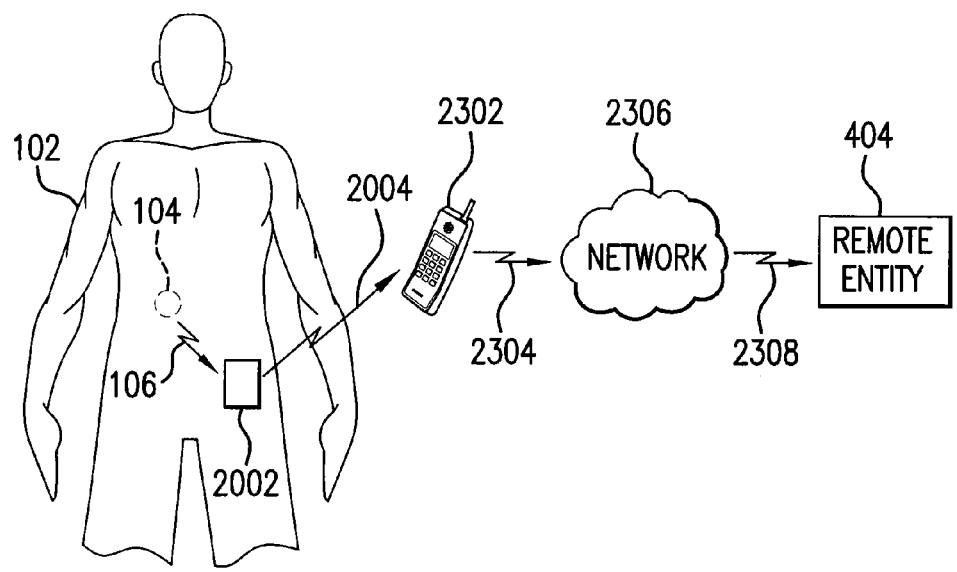
FIG. 23 is a block diagram of an exemplary communications network utilizing a sensor link module according to another embodiment of the present invention.

For example, FIG. 23 shows an embodiment where computing device 108 is a handheld device, such as a cell phone 2302. In an example Bluetooth embodiment, where a Bluetooth enabled cell phone 2302 is retrieving the sensor data from ingestible sensor device 104, cell phone 2302 may deliver a data packet via path 2204 through a cellular data network 2306 to remote entity 404, where remote entity 404 is a central medical diagnostic center or a central data storage facility. The sensor data may then be sent over this established link of cellular network 2306 to the medical diagnostic center, and the medical diagnostic center receives information via path 2308. If the sensor data is downloaded from sensor link module 2002 to a Bluetooth computer version of computing device 108, the data may be saved to storage of the computer (e.g., hard disk), a subsequently transferred over an Internet version of network 402 to the medical diagnostic center.

Power source 2210 provides power to elements of sensor link module 2002 that require power, such as control logic 2202, sensor communication module 2204, storage 2206, and remote communication module 2208. For example, power source 2210 may include one or more batteries that are rechargeable or non-rechargeable. Power source 2210 may also (or alternatively) include an interface for externally supplied power, such as standard A/C power.

Thus, in embodiments, sensor communication module 2204 includes a receiver (e.g., acoustic, RF, etc.) and remote communication module 2208 includes a transmitter. In this manner, information from ingestible sensor device 104 can be passed through sensor link module 2002 to computing device 108 and/or remote entity 404. In a further embodiment, sensor communication module 2204 includes a transmitter for transmitting a communication signal to ingestible sensor device 104 and/or remote communication module 2208 includes a receiver for receiving a communication signal from computing device 108. In this manner, information and/or control commands (e.g., instructions, a software/firmware upgrade, commands to activate certain sensors 202, etc.) from computing device 108 and/or remote entity 404 can be passed through sensor link module 2002 to ingestible sensor device 104.

Figure 24:
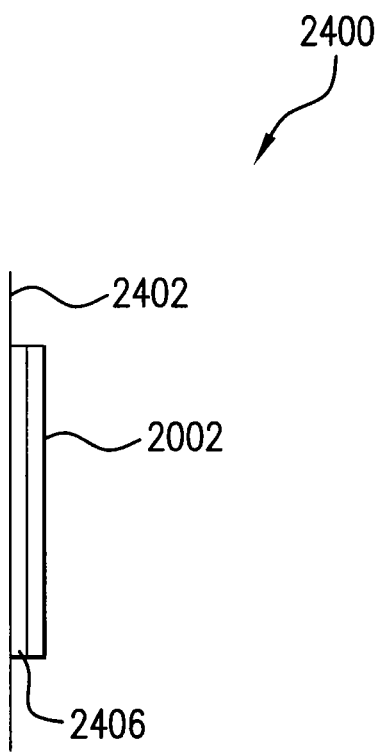
FIG. 24 is a block diagram of a sensor link module according to another embodiment of the present invention.

As described above, and shown in FIGS. 20, 21, and 23, sensor link module 2002 is coupled to human 102. Sensor link module 2002 may be coupled to human 102 in a variety of ways. For example, sensor link module 2002 may be directly attached to the skin of human 102, such as by an adhesive or a strap. FIG. 24 shows sensor link module 2002 incorporated in a patch 2400 for direct attachment to a surface 2402, such as skin, of human 102. As shown in FIG. 24, patch 2400 includes sensor link module 2002 and an adhesive layer 2406. Adhesive layer 2406 may include any type of adhesive material suitable for attaching sensor link module 2002 to surface 2402. For example, adhesive layer 2406 may include an adhesive commonly used in transdermal patches. In an embodiment, patch 2400 includes a release liner that covers adhesive layer 2406 prior to attachment to surface 2402. When ready to apply patch 2400 to surface 2402, the release liner is removed, exposing adhesive layer 2406. The exposed adhesive layer 2406 is applied to surface 2402, attaching patch 2400 to surface 2402.

In this manner, sensor link module 2002 may be coupled to human 102 for receiving communication signal 106 from ingestible sensor device 104. In an embodiment, a sensor link module 2002 may be attached to human 102 in one or more locations, including the head, neck, chest, back, abdomen, arm, leg, etc.

In an embodiment, sensor communication module 2204 of sensor link module 2002 includes a high sensitivity acoustic receiver. In an embodiment, sensor link module 2002 can function as a diagnostic device in addition to receiving sensor information from ingestible sensor device 104. Sensor link module 2002 can use the acoustic receiver to pick up the sounds of body functions from within human 102. Such functions include heart beat, breathing, blood flow, and digestion. These received sounds may be stored as data by sensor link module 2002, and may be used to augment sensor data received from ingestible sensor device 104.

As described above, in an embodiment, ingestible sensor device 104 can transmit an acoustic signal. By receiving the acoustic signal transmitted by ingestible sensor device 104, sensor link module 2002 may perform a type of ultrasound analysis based on the human interior generated acoustic signal from ingestible sensor device 104. As the acoustic version of communication signal 106 is transmitted from within human 102 from ingestible sensor device 104, signal 106 is transformed by attenuation, refraction, and reflection, as a function of the tissue of human 102 that signal 106 passes through. The transformed signal thus provides additional diagnostic information to sensor link module 2002, very much like a diagnostic ultrasound conveys diagnostic information that can be analyzed by a trained technician. The acoustic signal from ingestible sensor device 104 may be viewed as an "interior" ultrasound or "sonogram", which can be analyzed to extract additional diagnostic information regarding human 102. In an embodiment, information received by sensor link module 2002 regarding the interior ultrasound signal can be used to generate a graphical display of at least a portion of the interior of human 102. Further information regarding such acoustic imaging may be found in co-pending U.S. patent application Ser. No. 11/851,179, titled "Imaging and Locating Systems and Methods for a Swallowable Sensor Device", incorporated by reference herein in its entirety.

Figure 25:
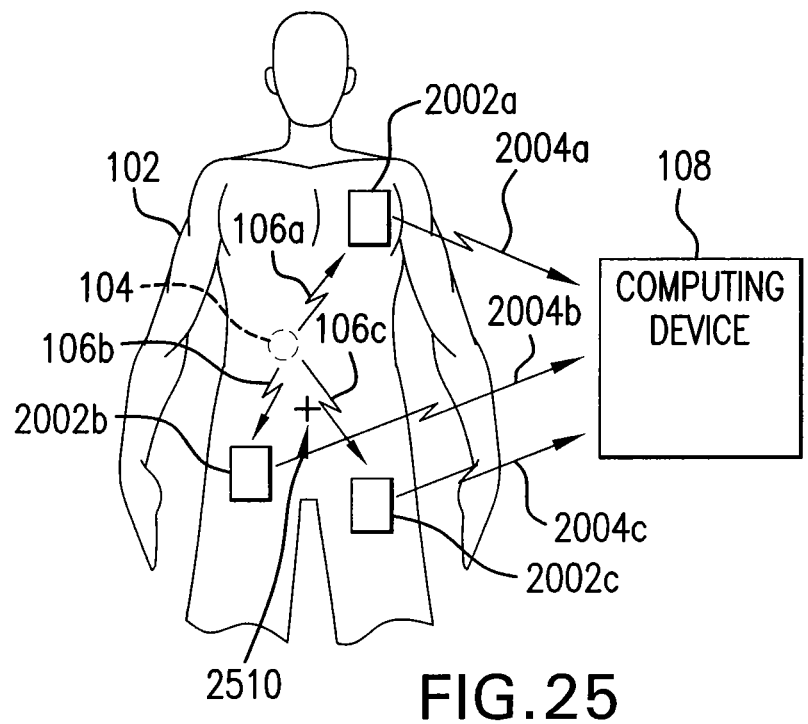
FIG. 25 is a block diagram of an exemplary communications network utilizing multiple sensor link modules according to an embodiment of the present invention.

For example, in an embodiment, multiple sensor link modules 2002 may be attached to human 102 at various locations in order to receive the interior acoustic signal from different angles. An amount of received acoustic information is proportional to the number of sensor link modules 2002 attached to human 102. For example, FIG. 25 shows an array of sensor link modules 2002a-2002c attached to human 102. The array of sensor link modules 2002 may be attached at specific locations on human 102 to increase, including maximizing, the acoustically received diagnostic information as well as to identify a specific location of the ingestible sensor device which can be used for identifying a location to a detection of a sensed material, or simply identifying a historical analysis of the track taken by the ingestible device and the speed of passage.

For example, the attachment of an array of sensor link modules 2002 to human 102, such as three sensor link modules 2002a-2002c, may enable "triangulation" or other location finding algorithms to be used to locate ingestible sensor device 104 in human 102. By locating ingestible sensor device 104 in human 102, a location of a sensed material in human 102 can be determined. Thus, this may enable a doctor, such as a surgeon, to ascertain the location of problem tissue, such as a tumor, a cancerous tissue, bleeding tissue, an ulcer, etc., so that the problem tissue can be treated, such as by removing the problem tissue, suturing the problem tissue, etc.

Such analysis of the acoustic data received by sensor link module 2002 may result in receiving a large amount of data, which may be processed by a signal processor. Sensor link module(s) 2002 may include a large amount of memory to store the acoustic data. Furthermore, or alternatively, sensor link modules 2002 may transmit the data to computing device 108 in "packets," before the memory of sensor link module(s) 2002 is full.

In an embodiment, sensor link modules 2002 may be placed onto human 102 with a predefined and absolute distance from reference point 110. Alternatively, a single sensor link module 2002 may be placed at a reference point 110. In these embodiments, data and information accumulated with location information may be re-composed or displayed on human 102 at a later date. Without such a fixed reference point, highly accurate location detection of sensor device 104 is only valid while sensor link modules 2002 are affixed or marked. In an example, sensor link module 2002 may be removed from human 102 after sensor device 104 passes out of the human 102. Accurate location of sensor device 104 is relative only to sensor link modules 2002. Once these are removed, the absolute location within human 102 is no longer known, although information regarding relative location from device 104 to sensor link modules 2002 can be stored indefinitely. Reference point 2510 may be, for example, a naval of human 102. In other embodiments, reference point 2510 may be a permanent mark (such as a tattoo), a semi-permanent mark (visible throughout an anticipated diagnosis and corrective cycle), or a written record of absolute distances from a multiple of other fixed body parts, such as sternum, clavicle, iliac crest, etc. Other selections of semi-permanent points of reference do not depart from the spirit and scope of this invention.

Information about the location of sensor device 104 may be sent by device 108 for permanent storage into remote entity 404 or network 402. Accurate location information coupled with sensor readings 202 can be displayed graphically to aid in a doctor's (or other) diagnosis. A display may include a three-dimensional trace of the path traveled by device 104 (x,y,z style representation, for example) as well as a linear distance of a path traveled by device 104. The linear distance may be, for example and without limitation, the distance from mouth 302 to device 104, or device 104 to anus 318, or both. In this embodiment, a doctor may make use of a three-dimensional location of an area of interest for a surgical procedure. Depending upon the diagnosis, a doctor may also utilize the linear distance to the area of interest to determine the appropriate use of an endoscopy or colonoscopy procedure. For example, if the area of interest is 25 linear feet from mouth 302 and 2 feet from anus 318, the doctor would choose a colonoscopy procedure for further diagnosis or treatment.

In an embodiment, data may be stored and physically transported to another processor, such as, for example and without limitation, a SIM memory card on external device 108 or sensor link module 2002. The memory card can then be removed to be placed in a computer at, for example, a doctor's office so that a wireless connection to a network is not required. In an alternative embodiment, sensor link module(s) 2002 are linked to computing device 108 by a wireless Bluetooth link. Computing device 108 stores the acoustic data received from sensor link module(s) 2002, collects the acoustic data into a file, and then send the entire data file over network 402 (e.g., the Internet) to remote entity 404, which may be a central diagnostic office for processing and analysis. In an embodiment where computing device 108 is a Bluetooth enabled phone, the phone may call the acoustic data in to the central diagnostic office as it is received, and the central diagnostic office may accumulate the data file until it is complete. Any number of combinations of device types and communication protocols for computing device 108, sensor link module 2002, and ingestible sensor device 104 are possible, and are encompassed by embodiments of the present invention, as would be understood by persons skilled in the relevant art(s) from the teachings herein.

In another embodiment, sensor link modules 2002 can be connected to computing device 108 via conductive paths such as with wires. Additionally, the package may be a flexible and wearable integrated unit comprising sensor link modules 2002, electrically conductive pathways 2004, computing device 108, and antennas (and/or appropriate shielding of these antennas) for use by computing device 108 (as in the case of cellular packet transmission). In this embodiment, computing device 108 may supply power through conductive pathways 2004 to sensor link modules 2002. In the case of a human use, the integrated package may include a comfortable cloth-like material, and may be in the format of a weight lifting belt or slimming girdle/undergarment.

Figure 26:
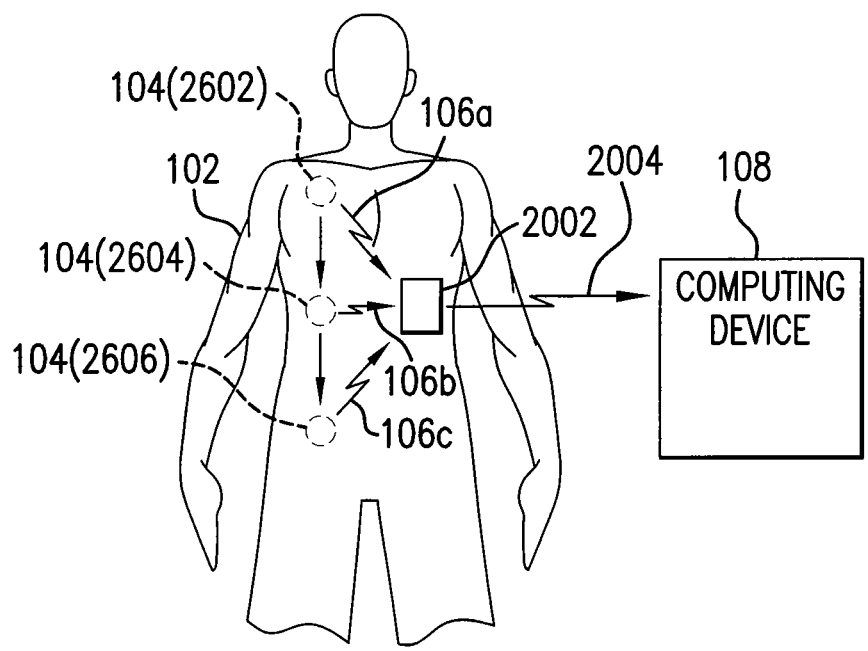
FIG. 26 is a block diagram of an exemplary communications network utilizing multiple ingestible capsules according to an embodiment of the present invention.

In an embodiment, human 104 may swallow a plurality of ingestible sensor devices 104 at a time, or within a relatively short time period, for a particular type of diagnostic test, such that the plurality of ingestible sensor devices 104 are in human 104 concurrently. For example, FIG. 26 shows human 102 having swallowed three ingestible sensor devices 104, shown as ingestible sensor devices 2602, 2604, and 2606. Ingestible sensor devices 2602, 2604, and 2606 respectively communicate with sensor link module 2002 using communication signals 106a-106c. When a plurality of ingestible sensor devices 104 are present in human 102, such as shown in FIG. 25, the ingestible sensor devices 104 may communicate with sensor link module 2002 in a variety of ways to avoid communication contention. For example, ingestible sensor devices 104 may use a simple Listen-Before-Talk (LBT) protocol to avoid contention. In another embodiment, ingestible sensor devices 2602, 2604, and 2606 may use different communication frequencies that can be received simultaneously by sensor link module 2002. In an embodiment, sensor link module 2002 may identify each ingestible sensor device 104 by its corresponding identification number, and may store the date and time.

In an embodiment, ingestible sensor devices 104 may be calibrated. For example, ingestible sensor devices 104 may be dispensed with a test kit (e.g., provided in a diagnostic kit sold/provided to the patient). The test kit may include one or more sensor link modules 2002. For calibration, for example, ingestible sensor devices 104 may be linked to a sensor link module 2002. An identification number and a sensor calibration (e.g., an output of each sensor 202, prior to being swallowed) of each ingestible sensor device 104 may be stored in the sensor link module 2002 and/or in an associated computing device 108. The sensor calibration data may be used in sensor link module 2002, computing device 108, and/or remote entity 404 to adjust the data output by the corresponding sensor.

In an embodiment, a medical diagnostic network system based on ingestible sensor devices 104 provides medical diagnostic tests to patients, wherever the patients are located, including remote locations. Based on a routine test or a specific patient complaint (e.g., provided by phone or internet) an attending physician at a medical center may send (e.g., via mail or other delivery system) a diagnostic kit to the patient, including ingestible sensor devices 104 specific to the diagnostic tests prescribed, and at least one sensor link module 2002. The diagnostic tests are performed as described herein using ingestible sensor devices 104. Based on the analysis of the diagnostic tests, medications and/or other treatment may prescribed and sent to the patient.

Thus, embodiments of the present invention simply existing diagnostic systems, making them cheaper and smaller, while at the same time providing more performance and capability. Embodiments describe herein may be more physician- and patient-friendly, where the patient testing can take place any time, anywhere. Ingestible sensor devices 104, with sensor link modules 2002 and/or computing devices 108, provide a low-cost, high performance platform that expand the number of medical conditions that can be evaluated beyond the limitations of current products. As a result, patients will require less invasive testing, for a wider array of conditions, with less risk of medical complication and pain.

Embodiments are more adaptable to busy patient lifestyles and physician office schedules, and enable and facilitate patient access to diagnostic testing. In embodiments, emerging health conditions can be identified early, when treatment can curb future problems. Elderly and pediatric patients, and patients in remote areas will now have access to physician counsel without the necessity of multiple office visits. A patient's health can be monitored and diagnosed, and a result of the monitoring and diagnostic tests can be provided to physicians or other health professionals quickly for review at any location, such as by the Internet or by cell phone call.

Furthermore, embodiments reduce a need for costly staff retraining and purchase of specialized equipment.

In embodiments, ingestible sensor devices 104 provide many advantages, including one or more of: lowering the cost of diagnosing and monitoring certain conditions and diseases; adapting diagnostic tests for today's active lifestyles; offering time-pressed patients diagnostic services when it is convenient for them, not just during inconvenient clinic hours; providing a simple, inexpensive, and mistake-proof, self administered diagnostic, especially useful for the elderly or disabled, improving accessibility to diagnosis and health monitoring for remote population groups, such as in rural and underserved areas, and; offering faster diagnosis, monitoring, and treatment for patients, which can prevent conditions from advancing to more serious levels.

In an embodiment, a medical electronic diagnostic interconnected on-line network system is provided. This system is configured to automate the process of sending ingestible sensor devices 104 in diagnostic kits to patients, and the retrieval and analysis of the resulting data. Thus, in an embodiment, this system provides a diagnostic kit to patient that includes ingestible sensor devices 104, configured based on a doctor's recommendation (e.g., for a general checkup, for a specific malady, a range of maladies, etc.). The patent applies one or more sensor link modules 2002 to himself/herself, as indicated in provided instructions, and swallows the ingestible sensor devices 104. Data from the ingestible sensor devices 104 is automatically provided via the sensor link module(s) 2002 to computing device 108 (e.g., a cell phone, computer, etc.), which may process the data, and forwards the data to remote entity 404 through network 402 (e.g., a phone network, computer network, etc.). Remote entity 404 (e.g., a computer and/or a physician) analyze the received data, and may make a further determination based upon the received data if necessary. For example, a further diagnostic test may be sent to the patient, medication (and/or other treatment, such as exercise, surgery, an in-office doctor visit, etc.) may be prescribed to the patient, information may be sent to the patient regarding the analysis, etc.

Embodiments of the present invention may provide many benefits to physicians and veterinarians, including one or more of the following: benefits over current existing tests, low relative procedure risk, low allergic reaction potential, low level of invasiveness, low infection potential, increased speed of results, ease of interpretation, no need for patient sedation, an outpatient setting is provided, the patient is more comfortable (e.g., at home, at work, on vacation), low cost of test, accurate testing, data may be presented in a variety of ways, ease of integration of received data with existing health medical records formats, low patient anxiety, high patient convenience, less office visits required, less additional equipment the physician needs to purchase, a low amount of additional training for staff.

Embodiments of the present invention may be used in a variety of medical, domestic, and other applications, including those described above, and further applications. For example, as described above, the baby boomer population may use the ingestible sensor devices, and related communication links, computing devices, networks, etc., to provide early and easy detection of health issues, and to preserve a better quality of life. The community of "health conscience" persons may desire to use the ingestible sensor devices, and related communication links, computing devices, networks, etc., to provide early and easy detection of health issues, and to help monitor and maintain a higher level of fitness, such as through enzyme detection, monitoring digestive process speed, etc. The well being of livestock may be monitored and improved by the ingestible sensor devices, and related communication links, computing devices, networks, etc., including the monitoring the quality of livestock meat, milk, etc., as well as providing early sickness detection and disease prevention. The monitoring of domestic pet health is improved by the ingestible sensor devices, and related communication links, computing devices, networks, etc., where both at home monitoring and veterinarian monitoring of pet health attributes, such as temperature, heart rate, breathing, etc. In an embodiment, ingestible sensor devices may be configured to be implantable for longer-term diagnostics for both domestic pets and livestock, including racing animals such as racing dogs and horses. Furthermore, in another embodiment, a couple desiring to become pregnant may use the ingestible sensor devices, and related communication links, computing devices, networks, etc., to be alerted to a best time to conceive on a real time basis over a several day period. Alternatively, a similar acoustic sensor system may be located on a vaginal suppository for hormonal and temperature monitoring.

Example Computer System Embodiments

In this document, the terms "computer program medium" and "computer usable medium" are used to generally refer to media such as a removable storage unit, a hard disk installed in hard disk drive, and signals (i.e., electronic, electromagnetic, optical, or other types of signals capable of being received by a communications interface). These computer program products are means for providing software to a computer system. The invention, in an embodiment, is directed to such computer program products.

In an embodiment where aspects of the present invention are implemented using software, the software may be stored in a computer program product and loaded into a computer system using a removable storage drive, hard drive, or communications interface. The control logic (software), when executed by a processor, causes the processor to perform the functions of the invention as described herein.

According to an example embodiment, an ingestible sensor device may execute computer-readable instructions to perform its functions. Furthermore, a sensor link module for communicating with the ingestible sensor device may execute computer-readable instructions to communicate with the ingestible sensor device. Still further, a computing device may execute computer-readable instructions to communicate with the ingestible sensor device and/or the sensor link module, and/or to process data obtained by the ingestible sensor device and/or sensor link module, as described above. Still further, a test kit and medical diagnostic network system may each execute computer-readable instructions to perform its functions.

CONCLUSION

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. An ingestible electronic sensor device, comprising:
a sensor configured to receive a stimulus inside a gastrointestinal tract of an animal, wherein the sensor is configured to output a signal having a characteristic proportional to the received sensor stimulus;
a communications module configured to transmit an acoustic signal modulated with the sensor output signal, the acoustic signal having a frequency in the range of 20 Hz to 16 KHz; and
a housing configured to have a size that is ingestible, wherein the housing substantially encloses the sensor and communications module.

2. The ingestible electronic sensor device of claim 1, wherein the housing is spherically shaped.

3. The ingestible electronic sensor device of claim 1, further comprising:
a power source that provides power to the communications module,
wherein the housing encloses the power source.

4. The ingestible electronic sensor device of claim 1, wherein the communications module comprises:
a modulator that modulates an acoustic carrier frequency with the sensor output signal to generate the acoustic signal.

5. The ingestible electronic sensor device of claim 4, wherein the communications module further comprises:
an amplifier that amplifies the acoustic signal.

6. The ingestible electronic sensor device of claim 1, further comprising:
a radiating element coupled to an output of the communications module.

7. The ingestible electronic sensor device of claim 6, wherein the housing is the radiating element.

8. An ingestible electronic sensor device, comprising:
a sensor configured to receive a stimulus inside a gastrointestinal tract of an animal, wherein the sensor is configured to output a signal having a characteristic proportional to the received sensor stimulus;
a communications module configured to transmit an acoustic signal modulated with the sensor output signal, wherein the modulated signal has an ultrasonic frequency; and
a housing configured to have a size that is ingestible, wherein the housing substantially encloses the sensor and communications module.

9. A medical diagnostic system, comprising:
an ingestible sensor device configured to be ingestible by an animal and includes:
a sensor configured to receive a sensor stimulus inside a gastrointestinal tract of the animal, wherein the sensor is configured to output a signal having a characteristic proportional to the received sensor stimulus;
a communications module configured to transmit an acoustic signal modulated with the sensor output signal, the acoustic signal having a frequency in the range of 20 Hz to 16 kHz; and
a housing configured to have a size that is ingestible, wherein the housing substantially encloses the sensor and the communications module, wherein the acoustic signal is an acoustic communications signal; and a sensor link module configured to receive the acoustic communications signal.

10. The medical diagnostic system of claim 9, further comprising:

a computing device, wherein the sensor link module is configured to transmit a second acoustic communication signal that includes at least a portion of data obtained by the sensor, and wherein the computing device is configured to receive the second acoustic communication signal.

11. The medical diagnostic system of claim 10, further comprising:

a remote entity, wherein the computing device is configured to transmit a third acoustic communication signal that includes data received from the sensor link module in the second acoustic communication signal, and wherein the remote entity is configured to receive the third acoustic communication signal.

12. The medical diagnostic system of claim 11, wherein the remote entity comprises a computer system.

13. The medical diagnostic system of claim 11, wherein the computing device transmits the third acoustic communication signal over a communications network, wherein the communications network includes at least one of a telephone network or the Internet.

14. The medical diagnostic system of claim 10, wherein the sensor link module transmits the second acoustic communication signal according to a Bluetooth protocol, an 802.11 protocol, or a Zigbee protocol.

15. A medical diagnostic system, comprising:

an ingestible sensor device configured to be ingestible by an animal and includes:

a sensor configured to receive a sensor stimulus inside a gastrointestinal tract of the animal, wherein the sensor is configured to output a signal having a characteristic proportional to the received sensor stimulus;

a communications module configured to transmit a communications signal modulated with the sensor output signal, wherein the communications signal is an ultrasound signal; and a housing configured to have a size that is ingestible, wherein the housing substantially encloses the sensor and the communications module; and a sensor link module configured to receive the communications signal.

16. The medical diagnostic system of claim 9, wherein the sensor link module is attached to the animal.

* * * * *